US008014756B1

(12) United States Patent
Henderson

(10) Patent No.: US 8,014,756 B1
(45) Date of Patent: Sep. 6, 2011

(54) MOBILE AUTHORIZATION SERVICE

(75) Inventor: Kenneth Henderson, Folsom, CA (US)

(73) Assignee: Intuit Inc., Mountain View, CA (US)

( * ) Notice: Subject to any disclaimer, the term of this patent is extended or adjusted under 35 U.S.C. 154(b) by 767 days.

(21) Appl. No.: 11/680,402

(22) Filed: Feb. 28, 2007

(51) Int. Cl.
*H04M 1/66* (2006.01)

(52) U.S. Cl. .......... 455/411; 709/225; 709/203; 705/44

(58) Field of Classification Search .................. 455/411, 455/412
See application file for complete search history.

(56) References Cited

U.S. PATENT DOCUMENTS

| | | | |
|---|---|---|---|
| 6,847,953 B2 | 1/2005 | Kuo | |
| 6,931,382 B2 | 8/2005 | Laage | |
| 7,058,611 B2 | 6/2006 | Kranzley | |
| 7,072,870 B2 | 7/2006 | Tallent | |
| 7,143,069 B2 | 11/2006 | Lacivita | |
| 2001/0044777 A1 | 11/2001 | Haley | |
| 2002/0032661 A1* | 3/2002 | Schuba et al. .................. | 705/64 |
| 2002/0082995 A1 | 6/2002 | Christie | |
| 2003/0101134 A1* | 5/2003 | Liu et al. .......................... | 705/39 |
| 2004/0054629 A1* | 3/2004 | de Jong et al. .................. | 705/51 |
| 2005/0086497 A1* | 4/2005 | Nakayama ..................... | 713/185 |
| 2006/0085337 A1* | 4/2006 | Conforti et al. .................. | 705/40 |
| 2006/0206709 A1* | 9/2006 | Labrou et al. .................. | 713/167 |
| 2007/0011044 A1 | 1/2007 | Hansen | |
| 2007/0027947 A1* | 2/2007 | Yokoyama ..................... | 709/203 |
| 2008/0120504 A1* | 5/2008 | Kirkup et al. .................. | 713/176 |
| 2009/0320088 A1* | 12/2009 | Gill et al. ........................... | 726/1 |

\* cited by examiner

*Primary Examiner* — Kamran Afshar
*Assistant Examiner* — Xiang Zhang
(74) *Attorney, Agent, or Firm* — Gunnison, McKay & Hodgson, L.L.P.; Philip McKay

(57) ABSTRACT

A mobile authorization service may be implemented as a web-based service, hosted on an authorization service server, and may exchange messages with various computing devices of subscribers to the service, including mobile communication devices. The service may be implemented as a software application executing on the server, and may include a client portion executing on subscriber computer systems and/or mobile communication devices, or subscribers may interact with the service using a text messaging application or a web browsing application. The service may receive an authorization request from a subscriber and may send a request message to an approver. The approver may send a reply message to the service indicating an answer. After authenticating the reply, the service may provide a response to the requester. The service may store information regarding authorization requests and responses. An authorization service subscriber account may be configurable for an individual or corporate subscriber.

30 Claims, 12 Drawing Sheets

| Menu 1  Menu 2  Menu 3  Menu 4 | Menu bar 252 |
|---|---|
| □ △ ⬠ ◇ ☆ | Tool bar 254 |
| /authorization\ /tab 2\ /tab 3\ request | Tab bar 256 | authorization request screen 220

Please enter the patient name:  | field 225 |

Please enter the diagnosis code: | field 226 |

Please enter the procedure code: | field 227 |

Please enter a comment (optional):

field 230

Please enter your personal id number: | field 235 |

Authorization request details:

field 240

✓ Submit 242

Display 250

*FIG. 2A*

| Menu 1 Menu 2 Menu 3 Menu 4 | Menu bar 252 |
| □ △ ⬠ ○ ☆ | Tool bar 254 |
| /authorization\ /tab 2\ /tab 3\ request | Tab bar 256 | authorization request screen 220

Please enter your employee id number:     field 225

Please enter the client account number:     field 226

Please enter the requested dollar amount:     field 227

Please enter the exception code:     field 228

Please enter a comment (optional):

field 230

Authorization request details:

field 240

✓ Submit 242

Display 250

*FIG. 2B*

MOBILE AUTHORIZATION SERVICE

BACKGROUND

More and more actions and transactions carried out each day require some level of authorization before they may be performed. For example, many medical procedures require pre-authorization from doctors, insurance companies and/or next of kin, before they may be performed. Similarly, many business transactions require pre-approval from one or more levels of management, from a financial officer, or from a human resources manager. For example, pre-approval is often required before money may be spent by a sales representative, contractor, or other employee (e.g., for business-related travel and entertainment expenses, goods and services to be provided, or training and recruiting expenses). In many cases, if circumstances change after the pre-authorization or pre-approval, an additional authorization or approval may be required before any changes may be made to a pre-approved budget or course of action. Traditionally, authorization has been implemented by routing signed documents between the interested parties, although more recently, electronic routing and signing of authorization requests are common within companies, such as through email or a company-wide transaction management system.

Traditional systems and methods for obtaining authorizations may be inadequate in emergency situations, however. For example, if a physician needs permission to perform emergency surgery on a child, but their parent is in a car on a highway two hours from the nearest city, the physician may not be able to obtain a signed medical authorization document before performing the procedure or, worse, may not be able to perform the surgery if authorization is not obtained.

Similarly, if contractor or sales representative determines that he or she needs additional funds to complete a task and there is a short window in which to complete the task, but the executive or manager from whom approval is needed is traveling and did not delegate signature authority, the contractor or sales representative may miss a deadline or a business opportunity that cannot wait until the executive or manager is back in touch with the office.

SUMMARY

Various embodiments of a system and method for facilitating remote approval of authorization requests through a trusted authorization service using mobile communication devices are disclosed. In some embodiments, a mobile authorization service may be implemented as a network-based or web-based service, hosted on an authorization service server, and may exchange messages and other information with various computing devices of subscribers to the service, including mobile communication devices (e.g., mobile phones, two-way pagers, or personal digital assistants or PDAs). The authorization service provides a trusted service to facilitate authorizations between subscribers to the service, so that requesters and approvers may be assured that authorization transactions completed using the service are valid.

In some embodiments, the authorization service may be implemented as a software application executing on an authorization service server. The authorization service application may in some embodiments include a client portion executing on one or more subscriber computer systems and/or mobile communication devices. In other embodiments, subscribers may interact with the authorization service application using another application executing on a subscriber computer system and/or mobile communication device, such as a text messaging application or a web browsing application. In still other embodiments, the service may be implemented in a peer-to-peer environment, with one or more of the peers hosting the service and one or more peers accessing the service as subscriber devices.

The authorization service application may be configured to receive an authorization request from a subscriber of the authorization service. The authorization request may include an indicator of a request type, an indicator of a requested action, a dollar amount, an account number, an identifier of the requester, and/or an identifier of an approver, in various embodiments. In some embodiments, the authorization request may be sent to the authorization service application from a mobile communication device (e.g., as a text message, email message, voice message, or image transmitted from a mobile communication device.)

In response to receiving the authorization request, the authorization service application may be configured to send a request message to one or more approvers indicating the authorization request. The authorization request may in some embodiments be sent to a mobile communication device. The authorization service application may in some embodiments determine an approver to which the request message should be sent dependent on information included in the authorization request.

An approver may send a reply message to the authorization service application indicating an answer to the request, which may include an approval, a rejection, a request for more information, and/or a comment, in various embodiments. The reply message may in some embodiments be sent to the authorization service from a mobile communication device. In some embodiments, the reply message may include authentication information identifying the approver (e.g., a personal identification number (PIN), a digital signature, an audio file comprising a voice command, a digital representation of a scanned thumbprint or retina, an image file comprising a scanned thumbprint or retina, or any other appropriate authentication information identifying the approver), and the authorization service application may be configured to authenticate the reply message before providing a response to the requester.

In response to receiving the reply message, the authorization service application may be configured to provide a response to the requester indicating the approver's answer. In some embodiments the response may be provided to the requester by sending a message to a mobile communication device.

After completing an authorization transaction, the authorization service application may be configured to store information regarding the authorization request, such as the authorization request, the request message, the reply message, and/or the response. In some embodiments, an authorization service subscriber account may be configurable for an individual or corporate subscriber. Because the authorization service is configurable, it may serve as a general-purpose authorization service appropriate for a wide variety of applications.

BRIEF DESCRIPTION OF THE DRAWINGS

FIGS. 2A-2C illustrate exemplary displays and user interfaces that may be provided by or used with a mobile authorization service, according to various embodiments.

While the invention is described herein by way of example for several embodiments and illustrative drawings, those skilled in the art will recognize that the invention is not limited to the embodiments or drawings described. It should be understood, that the drawings and detailed description thereto are not intended to limit the invention to the particular form disclosed, but on the contrary, the intention is to cover all modifications, equivalents and alternatives falling within the spirit and scope of the present invention as defined by the appended claims. The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). Similarly, the words "include", "including", and "includes" mean including, but not limited to.

DETAILED DESCRIPTION OF EMBODIMENTS

Various embodiments of a system and method for mobile authorization of authorization requests are described. In some embodiments, the system may provide a method and apparatus for a subscriber (e.g., a requester) to an authorization service to enter a request for authorization by another subscriber (e.g., an approver), capture a digital representation of an authorization response from the approver/user, and provide the authorization response to the initiator (e.g., the requester) of the request and/or to other interested parties. In some embodiments the system may include a method and/or apparatus to facilitate delegating authorizations, or may include various authorizing agents, or agents for reporting and/or billing of authorization transactions. In various embodiments, the requester or approver may interact with the authorization service via a mobile communication device (e.g., a mobile phone, pager, or personal digital assistant or PDA).

Figure 1:
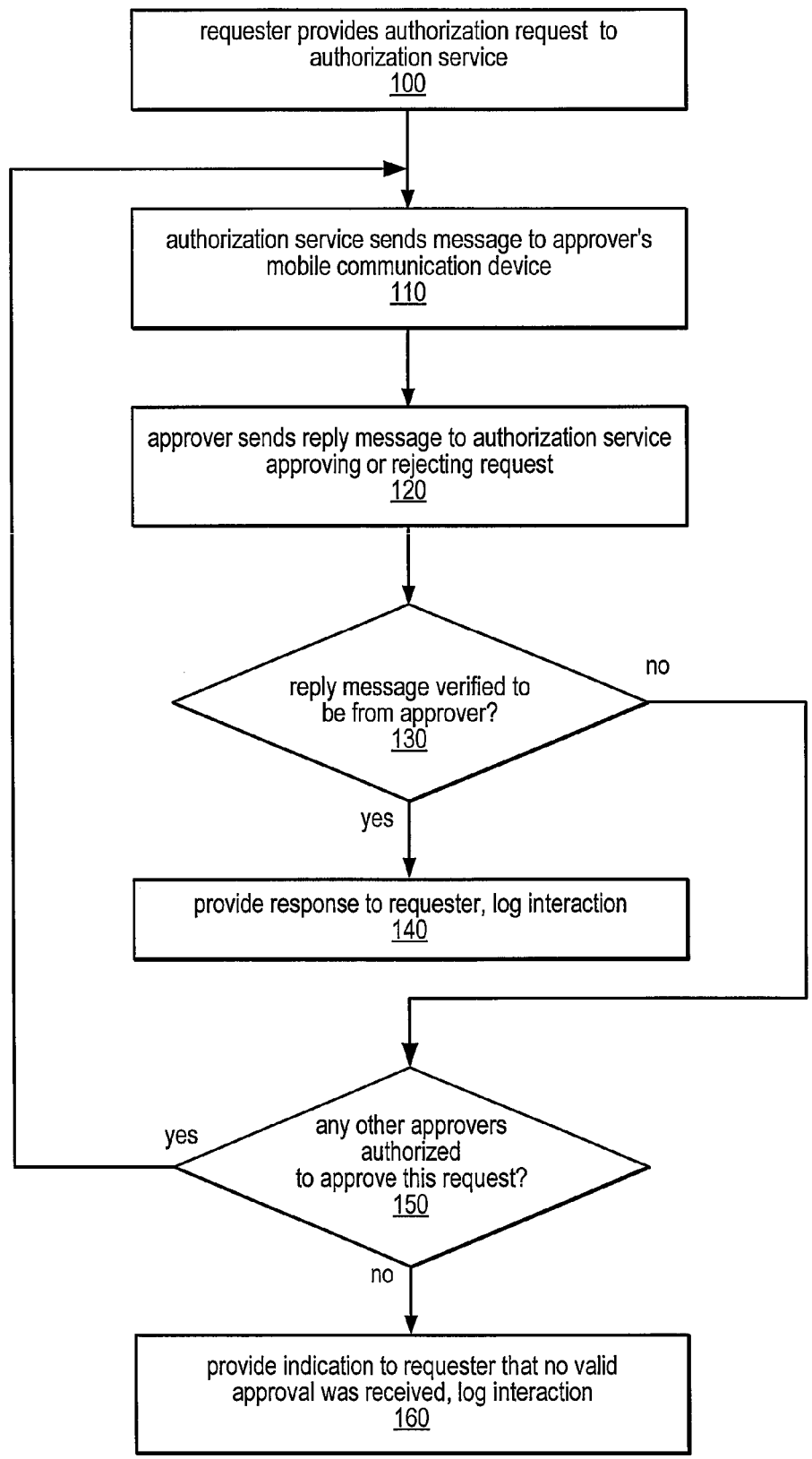
FIG. 1 illustrates a method for implementing a mobile authorization service, according to one embodiment.

An exemplary method for authorization using a mobile authorization service is illustrated in FIG. 1. In this example, a requester may initiate the authorization by providing a request for authorization to an authorization service, as in 100. The request may be used to seek authorization to spend money from a particular account, authorization to add money to a particular account, or authorization to perform a medical procedure, or may be used to seek authorization for any other action requiring pre-approval by one or more persons having the authority to approve the request.

The request for authorization may be provided to an authorization service hosted on a remote server, in some embodiments. For example, the authorization service may be a web-based service accessed by its customers (also called subscribers) through a Web browser. In some embodiments, the service may also be accessed by non-subscribers, such as by emergency service providers, customers or contractors of subscribers, or unregistered employees of corporate subscribers. Access by non-subscribers is described in more detail below. The request for authorization may be provided to the authorization service by filling out and submitting an online request form, in some embodiments. Various exemplary user input forms are described in more detail below. In other embodiments, any of various types of user input may be used to initiate a request for authorization, including, but not limited to, other graphical user interfaces (GUIs), voice input, menu-driven input, email messages, text messages, telephone calls, or fax messages.

In various embodiments, the request for authorization may include one or more of: a description of the request, an identifier of the request type, an identifier of an approver, an identifier of a requester, an identifier of a receiver of service (e.g., a patient or client) or a person on whose behalf a request is made, a dollar amount, an account identifier, an indication of priority and/or urgency, one or more comments, instructions for approval, instructions for replying, contact information for the requester and/or approver(s), and a date/time deadline for a reply. In some embodiments, one or more of these elements may be input by a requester, while others may be determined by the authorization service itself. For example, in some embodiments, one or more approvers may be specified in an authorization request, while in others the authorization service may determine one or more approvers for a given authorization request dependent on the type of request, the dollar amount of the request, the person or entity on whose behalf the request is made, or other information specified in the request.

In this example, the authorization service may receive the authorization request and may send a message to an approver's mobile communication device requesting authorization, as in 110. In some embodiments, the authorization service may be configured to create an electronic "ticket" or other electronic document dependent on information included in the authorization request and may send this document in the message to an approver. In some embodiments, the authorization service message may include some or all of the elements of an authorization request described above. For example, in some embodiments, the authorization service may send the approver a document selected or generated based on one or more fields input by the requester using an online request form. In other embodiments, the authorization service may send a message to the approver indicating that an authorization request is pending for the approver on the authorization service, and including instructions for logging into the authorization service to retrieve and/or respond to the request.

In this example, the approver may send a reply message to the authorization service indicating that he or she approves or rejects the request for authorization, as in 120. In some embodiments, the reply message may be sent using the mobile communication device to send a message to the server on which the authorization service is embodied. In other embodiments, the approver may use his or her mobile communication device to log into the authorization service in order to provide a reply (e.g., an approval or rejection of the request.) The reply message may in some embodiments include information usable by an authorizing agent to authenticate the identity of the responding approver and/or his authority to approve the request, such as an authorization code, an encryption key, a PIN, a digital signature, a voice command, a thumbprint or retinal scan, or any other indicator usable by various security mechanisms to verify the authenticity of message sender or to match the identity with his or her authority to approve requests.

As illustrated at 130, the authorization service may in some embodiments include one or more authorizing agents configured to authenticate the reply message and to verify that the reply message is from a valid approver. For example, in some embodiments, an authorizing agent may compare an authorization code, an encryption key, a PIN, a digital signature, a voice command, a thumbprint or retinal scan, or other indicator included in the approver's reply to one or more entries in a data store corresponding to the approver and/or the approver's authorization service account (e.g., a personal or corporate account.) If the approver's reply is authenticated and he or she is authorized to approve the request, the reply message may be determined to be valid.

If the reply message is verified to be from a valid approver, the authorization service may be configured to provide a response to the requester indicating whether or not the request was approved, as in 140. The response may be provided to the requester via a message (e.g., a text message, email message, or phone call), through a response screen of a graphical user interface, or by various other means. The response may include an identifier of the approver and/or comments from the approver in addition to the indication of approval or rejection of the request. In some embodiments, the response may be provided by updating a status field of an authorization request entry in a data store, so that the requester may see the change of status when examining a queue including one or more pending requests.

As illustrated at 140, the authorization service may also be configured to log the interaction associated with the request, once a valid response is received. For example, the authorization service may be configured to maintain copies of (or references to) each message sent or received regarding a given authorization request, from the requester's original input through the response provided back to the requester. In some embodiments, a logging function of the authorization service may be configured to create a file or database entry for each received authorization request and to add to the file or database entry each time a message involving the request is sent or received. In other embodiments, a separate file or database entry may be created for each interaction (e.g., each message sent or received) related to a received request that includes an identifier of the received request and/or a link to the received request.

In some embodiments, the authorization service may be configured to generate reports from logged information regarding a single request or a group of requests. For example, the authorization service may generate an audit log showing the status of a particular request at each step in the authorization process, including the time of each relevant interaction, the name of the requester and each approver, etc., or may generate a report summarizing the status for a group of related requests, in various embodiments. In some embodiments, such a report may be automatically generated following completion of the authorization process and/or in response to a query performed by a subscriber/customer at any time during or after processing of the request. While the logging function is illustrated in FIG. 1 as being performed at the end of the authorization process, in other embodiments, the logging described above may take place throughout the authorization process, such as after each relevant interaction.

In some embodiments, if the reply message is not authenticated, or if no reply is received within a specified period of time, the authorization service may be configured to determine if any other approvers are authorized to approve the request. This is shown as the negative exit from 130, and in 150. For example, a requesting organization (e.g., a corporation, department, or work group) may be a subscriber (e.g., a customer) of the authorization service and may have specified various rules or guidelines for an approval process or approval chain. In such cases, the authorization service may determine that another approver may be authorized to approve a request of the given request type or for the given dollar amount. In another example, the authorization service may be configured to send the authorization request to another approver in an approval chain if a reply message from one approver is not authenticated, or if more than one approval is required for the particular authorization request. If another approver is authorized to approve the request, the authorization service may be configured to initiate a repeat of the operations illustrated as 110-140 by sending the authorization request to the other approver.

If a reply message is verified to be from an authorized approver, but includes a rejection of the authorization request, the authorization service may in some embodiments be configured to send the authorization request to one or more other authorized approvers and to repeat the operations illustrated as 110-130 before providing a response to the requester indicating that the request was rejected. In other embodiments, any one approver's negative reply may be sufficient to reject the authorization request. In various embodiments, rules for obtaining one or more approvals for a particular request or request type may be configurable by subscribers, as described in more detail below.

If there are no other authorized approvers (if all operations 110-130 have been repeated for all authorized approvers), the authorization service may be configure to provide the requester with an indication that no valid approval was received, as in 160. In some embodiments, the requester may submit a follow-up authorization request (e.g., a modified request seeking approval for a different procedure, a different dollar amount, etc.) by modifying information entered on the original online request form and submitting a new authorization request including the modified information. In such embodiments, the operations illustrated in FIG. 1 and described above may be repeated for the new authorization request.

As illustrated at 160, the authorization service may also be configured to log the interaction associated with the request, even if no valid response is received. For example, the authorization service may be configured to maintain copies of (or references to) each message sent or received regarding a given authorization request, from the requester's original input through the negative response provided back to the requester. In some embodiments, a logging function of the authorization service may be configured to create a file or database entry for each received authorization request and to add to the file or database entry each time a message involving the request is sent or received. In other embodiments, a separate file or database entry may be created for each interaction (e.g., each message sent or received) related to a received request that includes an identifier of the received request and/or a link to the received request.

In some embodiments, the authorization service may be configured to generate reports from logged information regarding a single request or a group of requests. For example, the authorization service may generate an audit log showing the status of a particular request at each step in the authorization process, including the time of each relevant interaction, the name of the requester, the approver or approvers contacted, the amount of time waited before giving up on an approver, etc., or may generate a report summarizing the status for a group of related requests, in various embodiments. In some embodiments, such a report may be automatically generated following completion of the authorization process and/or in response to a query performed by a subscriber/customer at any time during or after processing of the request. While the logging function is illustrated in FIG. 1 as being performed at the end of the authorization process, in other embodiments, the logging described above may take place throughout the authorization process, such as after each relevant interaction.

In some embodiments, an authorization request may require more than one approval. For example, a subscriber/customer of the authorization service may specify that all requests must be authorized by two levels of management, or that authorization requests involving costs exceeding a particular dollar amount must be approved by two or more approvers. Similarly, an authorization to perform a given medical procedure on a minor or to release information about a minor may require approval by both parents, or by a parent and a primary care physician. In such embodiments, the authorization service may be configured to perform the set of operations illustrated as 110-160 of FIG. 1 for each approver in a chain serially, or in parallel for two or more approvers. The number and/or type of approvals needed may be configurable by subscribers or may be selectable when an authorization request is entered, in various embodiments.

In some embodiments, the authorization service may be configured to follow-up with an approver by providing a printed (or printable) copy of the authorization request, including an indication of the response received from the approver, and requesting that the approver sign the printed copy indicating that he or she did, in fact, provide the indicated response through the mobile authorization service, and return the signed copy to the authorization service for the interaction log.

In one exemplary use of a mobile authorization service as described above, a subscriber may receive a call from a hospital emergency room (through the mobile authorization service) on his mobile phone, requesting authorization to perform emergency surgery on his son. In this example, an authorization service application (e.g., hardware and software implementing the system and methods described herein) may be configured to patch the telephone call through, or otherwise convey the information, to the subscriber from the hospital. In one embodiment, the subscriber may give verbal authorization for the surgery and may enter his authorization service account PIN (personal identification number) using the touch pad on his mobile phone. In this example, the authorization service may automatically record the PIN and the verbal authorization from the conversation and may send a digitally signed facsimile (fax) of a standard medical authorization document to the emergency room so that the surgery may be performed right away. The authorization service may in some embodiments follow up on the transaction by sending a hard copy of the digitally signed medical authorization document and/or a transcript of the conversation to the subscriber's home address on file and/or may email a copy of the digitally signed medical authorization document and/or transcript to the subscriber's registered email account.

As noted above, the authorization service may in some embodiments allow individual subscribers/customers or subscribing entities (e.g., corporations, departments, work groups, or other types of organizations) to specify rules and/or guidelines for an approval process or approval chain for use when handling authorization requests initiated by the subscriber/customer and/or those that are to be approved by the subscriber/customer. Subscribers may be assured that the service will follow whatever approval rules have been set up for their account, and that approvals or other responses to authorization requests are valid.

These rules or guidelines may specify particular approvers that are authorized to approve requests, for example. In some embodiments, different approvers may be authorized to approve requests dependent on the type of a request, a dollar amount associated with a request, a department or account number associated with a request, a location of the requester (e.g., an employee's usual work location, or a location from which the employee sends a request while traveling), a location of an approver, a requester's job grade or title, an approver's job grade or title, or a supervisory relationship between a requester and one or more approvers.

The rules or guidelines specified by an authorization service subscriber/customer may in some embodiments include a chain of command for receiving approvals at two or more management levels, a delegation procedure used by the subscriber/customer (which may include an authorization request type for designating a different approver), or a mapping of requesters to approvers (e.g., by department number, by account number, by name, or by an employee identification number.) They may also include contact information for requesters and/or approvers, such as a primary and one or more secondary phone numbers (e.g., mobile phone numbers, home phone numbers, messaging service numbers, or work phone numbers), or one or more of a pager number, an email address, a user id (e.g., for a company-specific messaging server or service), a web page identifier (e.g., a URL to a public messaging service for sending messages to a mobile phone, PDA, or pager), a physical address, a mailing address, or any other contact information that may be usable by the authorization service for various purposes.

The rules and guidelines specified by an authorization service subscriber/customer may in some embodiments involve security details, such as specific encryption methods to be used in sending, receiving, and authenticating messages. They may in some embodiments include (or allow access to) a database of PINs, encryption keys, photographs, signature samples, digital signatures, thumbprint or retinal scans, voice prints, or other information that may be used to authenticate the identity of an approver. In some embodiments, the authorization service may include one or more default security methods for use when a subscriber/customer does not specify custom security features. For example, the authorization service may include a particular encryption algorithm for all messages unless a different mechanism is specified by a subscriber/customer for their messages. In some embodiments, security rules may include how or when to notify a subscriber/customer in response to detecting an unauthorized reply to an authorization request (e.g., in response to determining that a reply message was sent by someone other than the designated approver.)

In some embodiments, rules and guidelines specified by an authorization service subscriber/customer may in some embodiments include one or more timeout or retry values (e.g., specifying how many times an approver is contacted before giving up on reaching him or her, how many approvers are contacted before giving up on receiving approval, or how long the authorization service waits for a reply before trying again or contacting another approver.) In some embodiments, the authorization service may include one or more default timeout or retry values for use when a subscriber/customer does not specify one or more of these values.

Still other rules and guidelines for a subscriber/customer account may include billing procedures or selection of a standard or custom billing plan. For example, an individual or corporate subscriber may set up an account that includes a predetermined number of authorization transactions for a given subscription rate (cost). In another example, an individual or corporate subscriber may set up an account with an upfront and/or periodic retainer fee, and may pay for individual authorization transactions as they are used. The rules and guidelines for these subscribers may include payment terms, credit card or bank account numbers pre-authorized for transaction charges, purchase order numbers and details, billing addresses, etc.

The mobile authorization service described herein may in some embodiments be tied to the financial and/or accounting systems of one or more subscribers. For example, a corporate subscriber account may be configured to initiate the transfer of funds between various bank accounts and/or purchase orders (e.g., by wire transfer, using an on-line banking feature, or by transferring funds within a company's internal financial systems) in response to approval of authorization requests. In some embodiments, an authorization service subscriber's account may be associated with a fund, bank account, or line of credit managed by the authorization service from which money may be transferred in response to approval of an authorization request. For example, money may be electronically transferred to a contractor's bank account from a subscriber's authorization service account in response to approval of a request for additional funds. Each individual or corporate subscriber may define custom rules and guidelines for managing links to financial and accounting systems, in some embodiments. In some embodiments, the authorization service may offer one or more standard options for financial services such as those described above.

Other rules and guidelines that may be configurable by a subscriber may include the amount and type of data to be transmitted to particular types of mobile communication devices and other subscriber devices (e.g., a summary only, or a complete description of the request including any attachments), the amount and type of information to be displayed on particular types of subscriber devices, the application to be used to communication with the authorization service (e.g., a client portion of an authorization service application, a web browser application, a text messaging application, or a voice messaging application), or the amount and type of data to be stored regarding particular types of authorization transactions.

An authorization service subscriber may provide rules and guidelines, such as those described above, to the authorization service at the time an account is initially set up, or at one or more other times. In one embodiment, an authorization service subscriber may provide such rules and guidelines by entering account configuration information using a graphical user interface. The configuration information may apply to the subscriber's individual account, to a corporate account, or to another group of subscribers (e.g., all the employees of a particular department or work team, members of a family, or members of any group or organization whether or not they are included in a group subscription account). In some embodiments, an initialization process may involve requester(s) receiving permission and/or delegation authority from approver(s) that they will accept authorizations from the service. For example, a hospital may not accept a medical authorization from the service unless the hospital has on record a prior agreement from a client (e.g., a patient or a patient's guardian) allowing medical authorizations to be facilitated using the service. In other embodiments, a subscriber (e.g., a patient or patient's guardian) may have configured his or her own authorization service account so that the service is pre-approved for handling medical authorizations and/or other specific types of authorization transactions on his or her behalf. For other types of authorizations, such as company expense authorizations, specific pre-authorizations may not be required or may be less formal.

In some embodiments, a requesting entity may be a subscriber/customer of the authorization service, but an approver may not be. For example, a hospital or repair shop may be a subscriber/customer of the authorization service and may request authorization from a customer or client that is not a subscriber/customer of the authorization service (e.g., a spouse, parent, or car owner) before performing a particular procedure or service. In such embodiments, the requester may provide contact information (e.g., one or more phone numbers or email addresses) for their customer/client to the authorization service along with information about the request. In this example, the authorization service may be configured to contact the client/customer and to request that they register with the authorization service before approving the request.

In some embodiments, the approval process may include registering the client/customer (e.g., on a temporary or trial basis) by requesting identifying information (e.g., a voice sample, a thumbprint, account number with the requester's business, confirmation of an address, phone number, social security number, or birth date, etc.) from the client/customer that may be verified immediately or at a later time. For example, if the authorization request is related to a medical emergency, the authorization service may be configured to contact the client/customer for approval and request identifying information, but also to assume that the person contacted is the correct client/customer regardless of whether or not it is possible to immediately verify their identity and/or authority from the provided identifying information. In such embodiments, the authorization service may be configured to follow-up the initial contact by providing a printed copy of the authorization request, including an indication of the received response, and requesting that the approver sign the printed copy indicating that he or she did, in fact, provide the indicated response and return the signed copy to the authorization service for the interaction log. The authorization service may also be configured to offer an unregistered approver an opportunity to register as a subscriber/customer of the authorization service for future interactions with its sub scriber/customer base.

Similarly, in some embodiments, an authorization request may be provided to the authorization service by a non-subscribing requester. For example, a provider of emergency services that is not a subscriber to the authorization service may access the service to request a medical authorization, and may provide the service with as much information as they have about an approver (e.g., name, address, phone number). In such embodiments, the authorization service may be configured to contact the approver, whether or not the approver is a subscriber to the service, and to facilitate the medical authorization, as described herein. In some such embodiments, the authorization service may be configured to determine a name, address, phone number, or other contact information for an approver when the requester does not have enough information to locate the approver. For example, the authorization service may be configured to search an on-line directory to locate a parent or guardian in an emergency. In another embodiment, the authorization service may be configured to receive authorization requests from non-subscribing customers or contractors of a subscriber. For example, the authorization service may be configured to facilitate service requests for a subscriber's customers or the release of funds to a subscriber's contractors. In some such embodiments, the authorization service may be configured to offer an authorization service subscription to a non-subscribing requester.

In some embodiments, the authorization service may be configured to capture as much information as possible from non-subscribing requesters (e.g., emergency service providers or clients/customers of a subscriber) in order to log interactions with the non-subscribers for auditing purposes (e.g., to provide the requester with some evidence that the client/customer was contacted and responded, or to provide an approver with information about the source of a request from a non-subscriber). In one example, a phone conversation may be recorded and maintained with the interaction log. In another example, the authorization service may be configured to determine the location of a non-subscriber at the time of an authorization request or response (e.g., by determining a phone number from which a reply was received and/or a location of a mobile phone when used to reply.) Similar information may also be captured from subscribers/customers during an authorization transaction, in some embodiments.

As previously noted, an authorization service may be implemented as a web-hosted service and may include an authorization service server application as well as one or more client applications, which may execute on a subscriber's desktop computer, laptop computer, mobile communication device, or any other wired or wireless computing device, in different embodiments. Together, the server application and any client applications may be referred to herein as an authorization service application.

An authorization request may in some embodiments be provided to an authorization service application through a web-based graphical user interface. FIG. 2A, for example, illustrates an exemplary input screen that may be used to provide information about an authorization request to an authorization service application. In this example, as in FIGS. 2B, 3, and 4, a display (in this case, display 250) may include one or more of, but is not limited to, a menu bar (e.g., menu bar 252), a tool bar (e.g., tool bar 254), and a tab bar (e.g., tab bar 256). In the example illustrated in FIG. 2A, menu bar 252 may provide one or more menus for accessing various functionalities of an authorization service application via user-selectable interface items (i.e., menu selections). Tool bar 254 may provide one or more tool icons for accessing various tools of the authorization service application's web-based interface. Tab bar 256 may provide one or more tabs for switching between various views presented to an authorization service subscriber/customer.

In the example illustrated in FIG. 2A, the currently selected tab displays an authorization request screen 220, specifically, an authorization request screen that may be used to request authorization to perform a medical procedure. In this example, the illustrated screens may be displayed on a desktop computer at a hospital, which may be connected with a web-based application server through a web browser or may be executing a client application portion of the authorization service application locally. Note that authorization request screen 220 is intended to be representative of both an authorization request document presented as a template for data entry by a requester, and data entry displays that include input fields for entering data and information to be transferred into authorization request documents and/or interaction logs. As illustrated, authorization request screen 220 may include multiple fields for user input, as well as one or more display fields.

In this example, fields 225, 226, 227, and 235 (specifying the patient's name, a code indicating a diagnosis, a code indicating the procedure for which approval is requested, and an identifier of the requester (e.g., a doctor or healthcare administrator) may be required fields for all medical authorization requests. In various embodiments, data may be entered into one of these fields by selecting a field and typing in data, by selecting a field and a data value for the field using a pull-down menu, or by any other suitable means. In some embodiments, an optional comment field (e.g., comment field 230) may be provided so that the requester may enter other information that may be provided to an approver to further clarify the diagnosis and/or recommended procedure, or to provide contact information for an approver (e.g., for a parent who is not a subscriber/customer of the authorization service.)

In some embodiments, all the information that is to be provided to an approver may be entered by the requester. In other embodiments, an approver may be presented with a subset of the information entered by the requester and/or with additional information. For example, the authorization service application may be configured to select one or more predefined descriptions, documents, or other attachments (e.g., a graphical representation of an x-ray or other test data) dependent on the information entered by the requester, and to display or otherwise provide this additional information to an approver. This additional information may, for example, include the patient's name and/or health history (corresponding to the patient number entered), a description of a diagnosis (corresponding to the diagnosis code entered), a description of the recommended procedure (corresponding to the procedure code entered), or the name of the requester and/or healthcare professional who is recommending or who may be performing the recommended procedure (e.g., based on the personal id entered, the procedure to be performed, the doctor assigned to the patient's case according to the patient's information, etc.) In some embodiments, the additional information (e.g., descriptions, documents, or other attachments) may be displayed in field 240 so that it may be reviewed by the requester before the authorization request is submitted.

In some embodiments, the authorization service application may be configured to automatically generate an authorization request document or display dependent on the information entered by the requester and/or information accessible to the authorization service application, such as standard descriptions of diagnoses and/or procedures, patient information maintained in a hospital database, a mapping of doctors or administrators to personal identifiers, the current date and time, or contact information for one or more approvers (e.g., a parent/guardian, a insurance representative, or a hospital administrator, depending on the number and type of approvals needed to perform the procedure.)

In some embodiments, the generated authorization request document or display may be displayed in field 240 so that it may be reviewed by the requester before the authorization request is submitted. In some embodiments, display field 240 may present the requester with a representation of what an approver will see when the authorization request is presented to the approver. In other embodiments, field 240 may be an additional input field into which the requester may enter more details about the diagnosis, recommended procedure, authorization process, status of the request, or any other information that may be useful to include in an authorization request. In still other embodiments, field 240 may be used to display information regarding the status of the pending authorization request, and the authorization service application may be configured to automatically update this field as the authorization request is processed (e.g., tracking the request as it is sent to one or more approvers and/or indicating the response from each approver as it is received by the authorization service application, so that each approver may see the current status of the authorization request at the time he or she receives the authorization request.)

After filling in all required input fields (and possibly one or more optional fields) of the authorization request, a requester may submit the authorization request to the authorization service application. In the example, illustrated in FIG. 2A, the authorization request may be submitted by selecting the "submit" checkbox 242. In other embodiments, the authorization request may be submitted using a menu selection, radio button, keystroke shortcut, command line input or any other user interface suitable for command input. As previously noted, the authorization service application may in some embodiments provide the requester with a preview of the complete authorization request for review before the requester submits the authorization request.

Note that another tab of display 250 may be selected to display a screen for entering account configuration information (not shown.) Such an input screen may include a graphical user interface similar to that illustrated in FIG. 2A, including one or more input fields (similar to fields 225, 226, and 227) for entering configuration information for a subscriber's authorization service account, as described herein, and/or one or more display fields (similar to field 240) for viewing default or selected values of various configuration options for the subscriber's account. A configuration input screen may also include an account id field (similar to personal id 235), a comment field (similar to field 230) and a "submit" checkbox (similar to 242), in some embodiments.

In additional to facilitating medical authorizations, an authorization service such as that described herein may be applied to other types of authorizations, such as business expense authorizations. For example, if a sales representative is out entertaining potential clients and thinks that one more bottle of expensive wine will seal the deal, but he has exceeded his standard per diem, he may use the mobile authorization service to request authorization to spend the additional money. In this example, the sales representative may access the authorization service using his PDA and may enter a description of the expense and the dollar amount. Based on his company's profile, the dollar amount of the request may require authorization from his boss's boss. In this example, the authorization service may first send a message to his boss's mobile phone. If his boss agrees with the request, he may enter his authorization PIN and reply to the message. The authorization service may authenticate the message and validate the PIN. The authorization service may then forward the authorization request to his boss's boss on his PDA. If his boss's boss approves of the request, he may enter his authorization PIN and reply to the message. The authorization service may authenticate the message and validate the PIN, and then may send a reply to the employee's PDA letting him know that the request was approved.

In another example, a contractor may determine that he needs $600 worth of materials, but he is only authorized to purchase $500. The contractor may enter a purchase order and may send an authorization request to release an additional $100 in funds from the project account for the purchase order. The project supervisor may receive the authorization request on his mobile phone and may swipe his thumbprint on his mobile phone's thumbprint reader and enter his PIN. Once the authorization service authenticates the message and validates the PIN, the funds may be immediately released to the contractor.

In these examples, both the authorization requests and the approvals may be initiated from a mobile communication device, rather than from a desktop computer or other wired or wireless computing system configured to operate in a fixed position. In these examples, the messages sent between the requester, approver, and authorization service may simply be entered as text messages sent to or from a particular email address corresponding to a company's authorization service subscription account, which would receive the messages and respond accordingly, or they may be entered using a graphical user interface (e.g., by using a web browser application on a mobile phone or PDA to access the company's authorization service account on an authorization service server, or by executing a client portion of the authorization service application locally on the mobile communication device.)

An exemplary authorization request screen 220 suitable for requesting a business expense authorization is illustrated in FIG. 2B. In this example, as in the example illustrated in FIG. 2A, display 250 may include one or more of, but is not limited to, a menu bar (e.g., menu bar 252), a tool bar (e.g., tool bar 254), and a tab bar (e.g., tab bar 256). As in the example illustrated in FIG. 2A, menu bar 252 may provide one or more menus for accessing various functionalities of an authorization service application via user-selectable interface items (i.e., menu selections). Tool bar 254 may provide one or more tool icons for accessing various tools of the authorization service application's web-based interface. Tab bar 256 may provide one or more tabs for switching between various views presented to an authorization service subscriber/customer.

In the example illustrated in FIG. 2B, the currently selected tab displays an authorization request screen 220 that may be used to request authorization for a business expense (e.g., a request to add money to an expense account, to spend money allocated to a particular account, to spend money in pursuit of a new account or agreement, etc.) As illustrated, authorization request screen 220 may include multiple fields for user input, as well as one or more display fields.

In this example, fields 225, 226, 227, and 228 (specifying the requester's employee number, a client account number, a requested dollar amount, and an exception code) may be required fields for business expense authorization requests. In various embodiments, data may be entered into one of these fields by selecting a field and typing in data, by selecting a field and a data value for the field using a pull-down menu, or by any other suitable means. In some embodiments, an optional comment field (e.g., comment field 230) may be provided so that the requester may enter additional information that may be provided to an approver, such as details about requested expense (e.g., how, where, when, and on what the money is to be spent, or a projected outcome if the expense is approved or denied), or to provide an identifier and/or contact information for an approver (e.g., for an approver who is not an employee of the requester's company and/or who is not a subscriber/customer of the authorization service, or for an approver other than one specified in company rules or guidelines accessible by the authorization service.)

As in the previous example, in some embodiments, all the information that is to be provided to an approver may be entered by the requester. In other embodiments, an approver may be presented with a subset of the information entered by the requester and/or with additional information. For example, the authorization service application may be configured to select one or more predefined descriptions, documents, or other attachments (e.g., client or account information, or a graphical representation of sales data relevant to the client or account) dependent on the information entered by the requester, and to display or otherwise provide this additional information to an approver. This additional information may, include, for example, the name of the requester (e.g., based on the employee id number entered), the client or account name, account history, or the current budget associated with the client or account (corresponding to the client account number entered), a description of the type of exception (e.g., create a new purchase order or account for existing client, create a purchase order or account for potential new client, add money to an existing expense account or purchase order, spend money from an existing account or purchase order, take a business trip, extend a business trip beyond its pre-approved length, delegate approvals to another manager, etc., dependent on the exception code entered). In some embodiments, the additional information (e.g., descriptions, documents, or other attachments) may be displayed in field 240 so that it may be reviewed by the requester before the authorization request is submitted.

In some embodiments, the authorization service application may be configured to automatically generate an authorization request document or display dependent on the information entered by the requester and/or information accessible to the authorization service application, such as standard descriptions of exception codes or expense request procedures, client information maintained in a corporate database, a mapping of employees to employee identifiers, the current date and time, or contact information for one or more approvers (e.g., a supervisor, managers at one or more levels, or a financial officer, depending on the number and type of approvals needed to authorize the requested expense.)

In some embodiments, the generated authorization request document or display may be displayed in field 240 so that it may be reviewed by the requester before the authorization request is submitted. In some embodiments, display field 240 may present the requester with a representation of what an approver will see when the authorization request is presented to the approver. In other embodiments, field 240 may be an additional input field into which the requester may enter more details about the client or potential client, the requested expense, any alternatives to consider, the status of the request, or any other information that may be useful to include in an authorization request. In still other embodiments, field 240 may be used to display information regarding the status of the pending authorization request, and the authorization service application may be configured to automatically update this field as the authorization request is processed (e.g., tracking the request as it is sent to one or more approvers and/or indicating the response from each approver as it is received by the authorization service application, so that each approver may see the current status of the authorization request at the time he or she receives the authorization request.)

After filling in all required input fields (and possibly one or more optional fields) of the authorization request, a requester may submit the authorization request to the authorization service application. In the example, illustrated in FIG. 2B, the authorization request may be submitted by selecting the "submit" checkbox 242. In other embodiments, the authorization request may be submitted using a menu selection, radio button, keystroke shortcut, command line input or any other user interface suitable for command input. As previously noted, the authorization service application may in some embodiments provide the requester with a preview of the complete authorization request for review before the requester submits the authorization request.

Figure 2C:
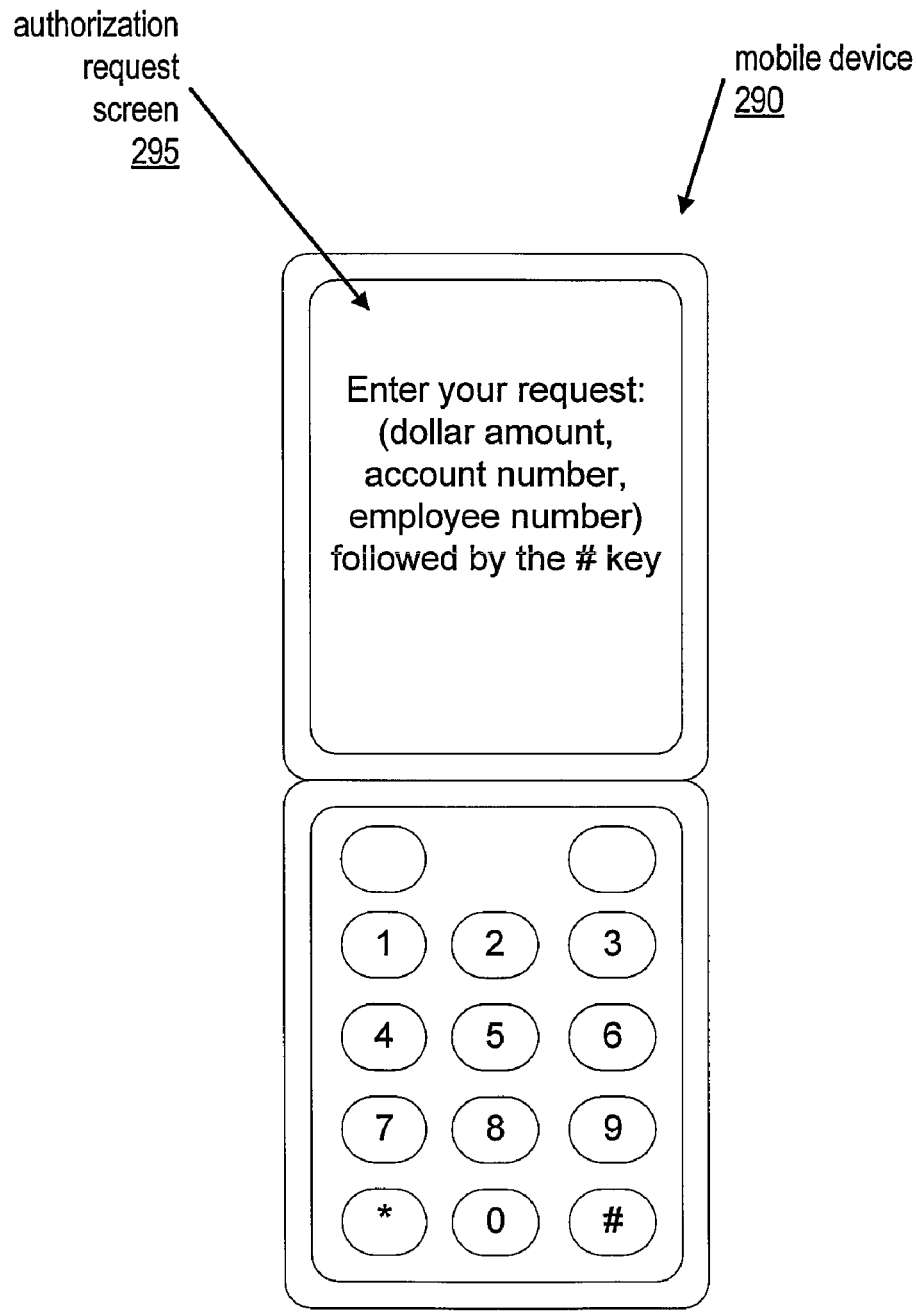

In some embodiments, a mobile communication device used by a requester may include a simpler display and/or interface than display 250 illustrated in FIGS. 2A and 2B. For example, an authorization request may be provided to an authorization service by sending a text message to a particular phone number or email address, in some embodiments. FIG. 2C illustrates an exemplary authorization request screen 295 displayed on a mobile communication device 290 for such an embodiment. In this example, in response to selecting a particular function, phone number, or email address, a requester may be prompted to enter an authorization request as a text message according to a particular format (e.g., a comma separated list including a dollar amount, an account or project number associated with the request, and an identifier of the requester.) In this example, the authorization request is followed by the pound key ("#"), which initiates submission of the request. The format of such an authorization request text message, as well as any keypad commands or functions used by a requester, may be configurable by a subscriber, in some embodiments.

Figure 3A:
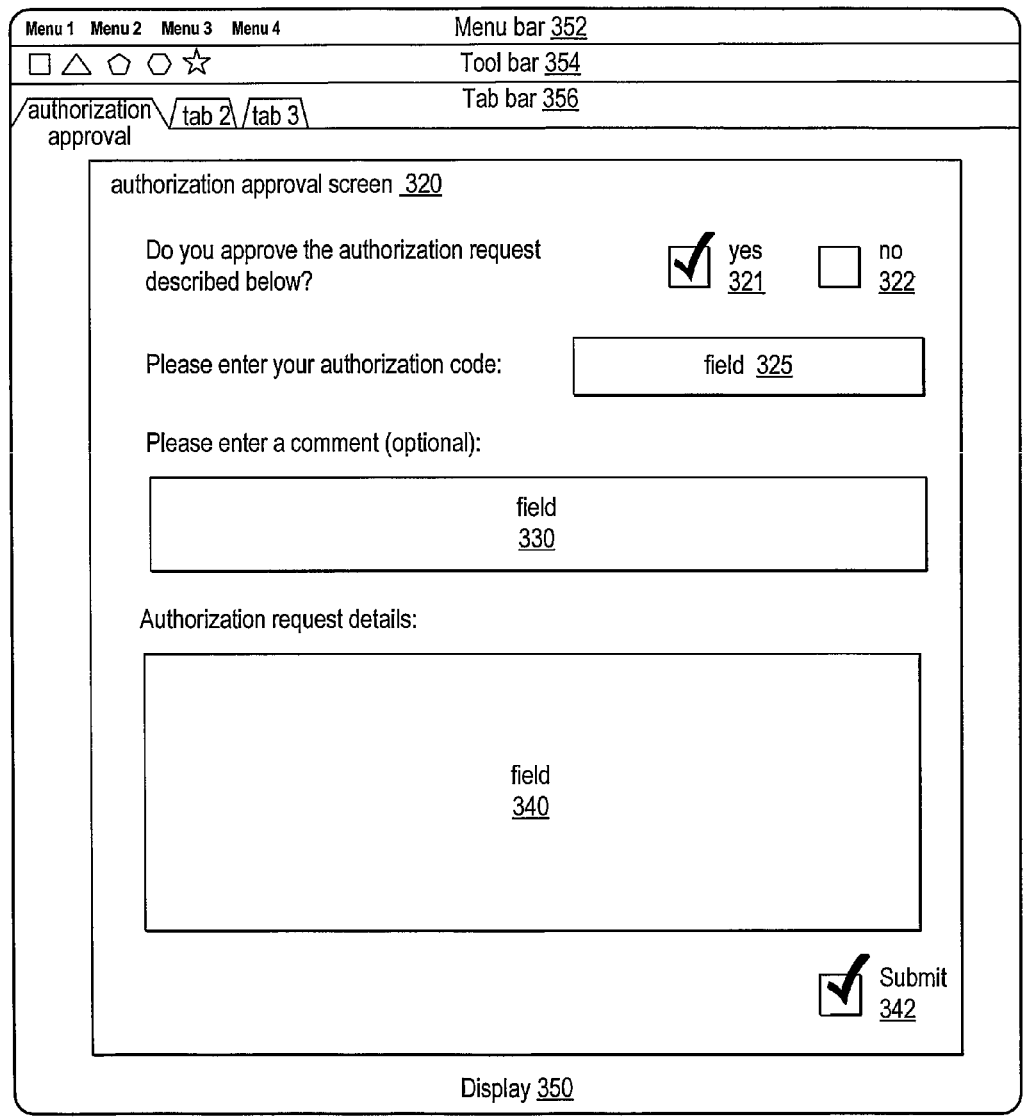
FIGS. 3A-3D illustrate exemplary displays and user interfaces that may be provided by or used with a mobile authorization service, according to various embodiments.

As previously described, an authorization request may in some embodiments be sent to an approver via his or her mobile communication device (e.g., a mobile phone, pager, or PDA). In some embodiments, the authorization request itself (or a portion thereof) may be sent to and displayed on the mobile communication device, while in other embodiments a message may be sent to the mobile communication device instructing the approver to log onto a web-based authorization service to retrieve and/or display an authorization request. An exemplary display (display 350) for presenting an authorization request to an approver is illustrated in FIG. 3A. In this example, display 350 may include a menu bar 352, a tool bar 354, and a tab bar 356, similar to the menu bar 252, tool bar 254, and tab bar 256 described above. In other embodiments, a display 350 on a mobile communication device may include more, fewer, or different graphical user interface elements than those illustrated in FIG. 3A.

In the example illustrated in FIG. 3A, an authorization screen 320 may be presented to an approver on display 350. In this example, authorization screen 320 may include one or more input fields (e.g., fields 321, 322, 325, and 330) and one or more display fields (e.g., field 340). In some embodiments, when an approver receives an authorization request, a portion of the request (e.g., a summary or brief description of the request) may be presented in a display field, such as display field 340. This brief description may correspond to a description entered by the corresponding requester (e.g., in a comment field 230 or other input field) or may be generated by the authorization service application dependent on the contents of one or more fields of the authorization request (e.g., dependent on one or more of a diagnosis code, a procedure code, an exception code, a dollar amount, a client account number, etc.) In other embodiments, the complete authorization request (with or without attachments) may be presented to the approver in display field 340. As previously noted, the information presented to the approver in display field 340 may correspond to a preview presented to the requester before the authorization request was submitted.

Information presented to an approver may, in various embodiments, include one or more of: a description of the request, an identifier of the request type, an name or identifier of the requester, a name or identifier of a receiver of service (e.g., a patient or client) or a person on whose behalf a request is made, a dollar amount, a client or account name or identifier, an indication of priority and/or urgency, one or more comments, instructions for approval, instructions for replying via the mobile communication device or other means, contact information for the requester and/or any other approver(s), and a date/time deadline for a reply.

As illustrated in FIG. 3A, input fields presented to an approver may include inputs usable to select a response to the request, such as radio buttons 321 ("yes") and 322 ("no"). If the approver is ready to approve or reject the request based on the information presented, he or she may in some embodiments select, or otherwise enter, a response and then may select a "submit" operation, such as by selecting radio button 342. In other embodiments, the approver may not be able to submit his or her response until or unless he or she enters information usable for verifying his or her identity and/or authority, as described below.

In some embodiments, an input field may be usable by the approver to enter an authorization code in order to verify his or her identity and/or authority to approve the received authorization request. For example, FIG. 3A illustrates an authorization code field 325 into which an approver may enter a password, PIN, encryption key, or other authorization code, which may in some embodiments be specific to a particular request type, a purchase order, account or client, department or other organization level, or other sub-set of the authorization requests for which the approver is an authorized approver. As previously noted, the authorization service application may be configured to verify the identity of the approver and/or the authority of the approver to approve the particular request before replying to the requester with the approver's response. In such embodiments, the authorization service application may use the authorization code entered (and/or other information, such as the location of the approver's mobile communication device, and the rules or guidelines for the approval process of the particular subscriber/customer) for its verification/authentication process and/or for logging the response in a trace or audit log for the particular authorization request. In some embodiments, a mobile communication device may be configured to capture and/or transmit other types of identifying information for the approver, such as a signature, voice print, thumbprint scan, or retinal scan, to be used in the authorization service's verification/authentication process.

In the example illustrated in FIG. 3A, once the approver has entered a response and/or one or more comments or questions, along with an authorization code, he or she may select a "submit" operation, such as by selecting radio button 342. Selecting the submit operation may cause a reply message to be sent to the authorization service application (e.g., as a text message from the mobile communication device, or through a web browser interface.)

In some embodiments an additional input field (e.g., a menu selection or radio button) may allow the approver to request more information before approving the request. For example, an approver may select a menu item "request more information", may enter one or more specific questions in comment field 330 using a keypad of his or her mobile communication device (e.g., "What are the consequences of rejecting this additional expense?" or "What is the patient's blood pressure?"), and may submit his or her response without selecting either of radio buttons 321 ("yes") or 322 ("no"). In some embodiments, in response to the request for more information, the authorization service application may be configured to send the complete authorization request and/or any attachments to the approver's mobile communication device and/or to display the complete authorization request and/or attachments in display 340, if the approver was initially presented only with a summary or other brief description of the request.

In another example, an approver may select a menu item "request more information", may enter one or more specific questions in comment field 330 using a keypad of his or her mobile communication device (e.g., "What are the consequences of rejecting this additional expense?" or "What is the patient's blood pressure?"), and may submit his or her response without selecting either of radio buttons 321 ("yes") or 322 ("no"). In such embodiments, in response to the request for more information, the authorization service application may be configured to send a message to the requester relaying the request for more information, and including the approver's question(s). The requester may then enter additional information into the authorization request (e.g., the requester may edit the original request to include answers to the approver's questions) and may re-submit the request. When the approver receives the edited request, he or she may then be ready to approve or reject the request.

Figure 3B:
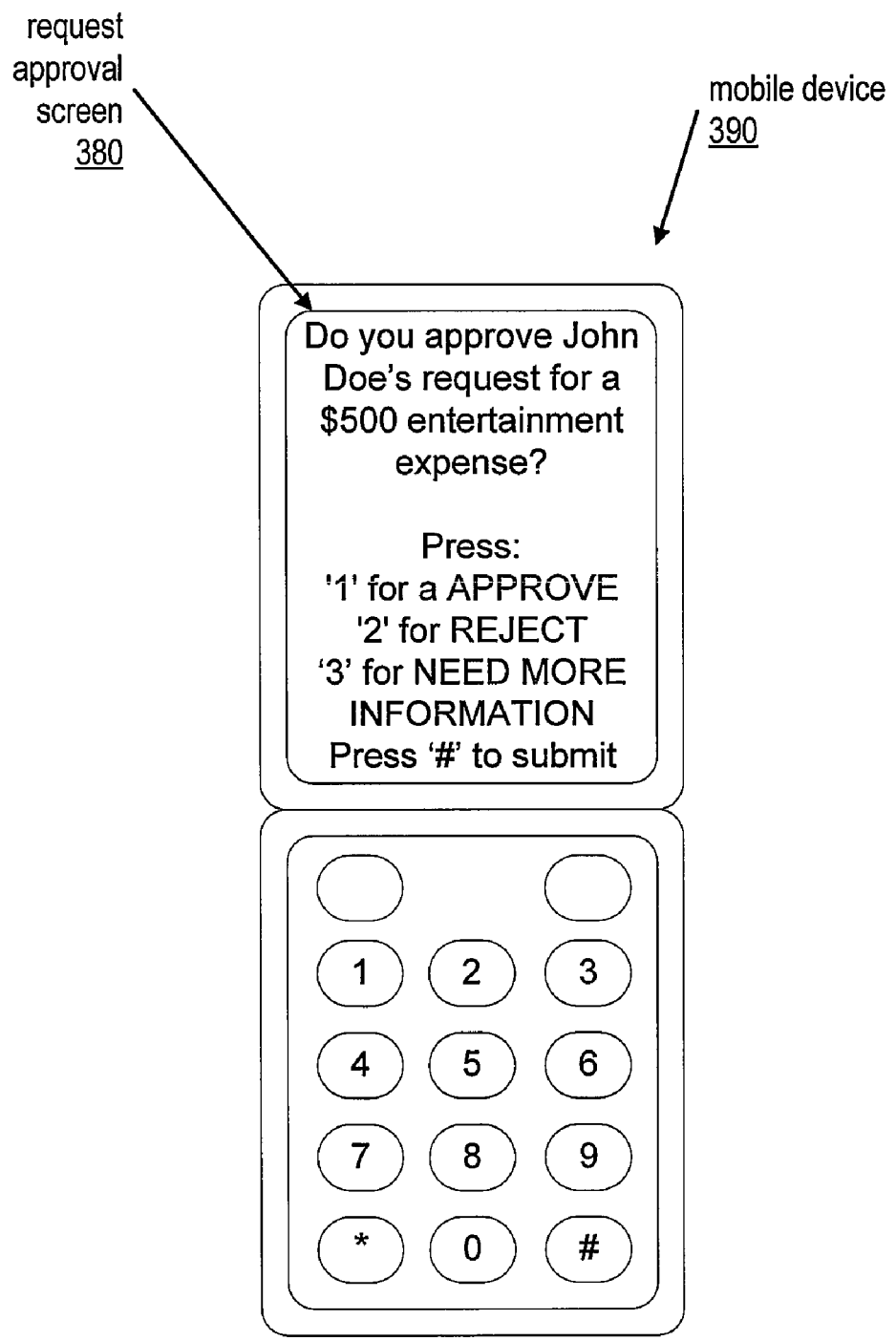
Figure 3C:
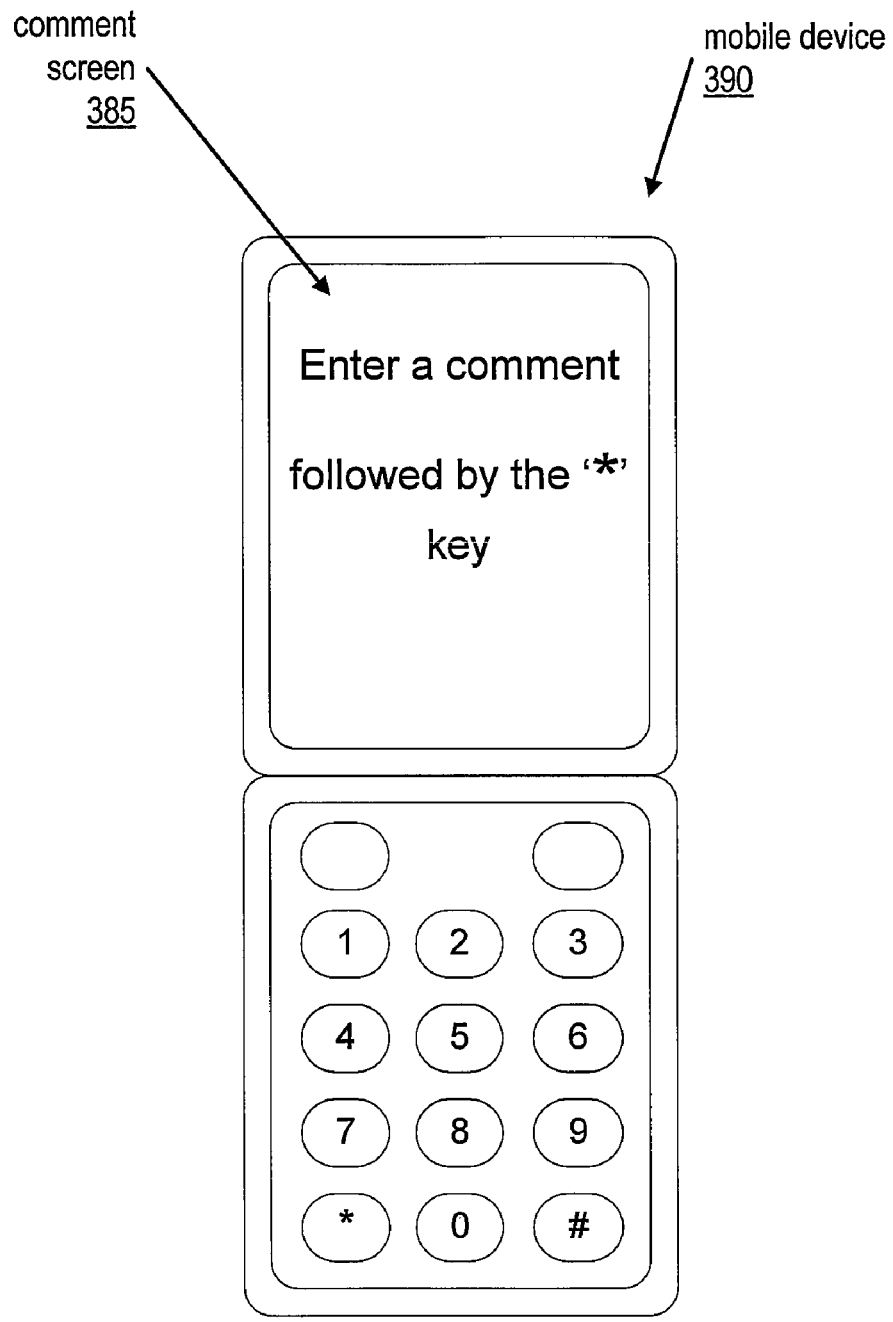
Figure 3D:
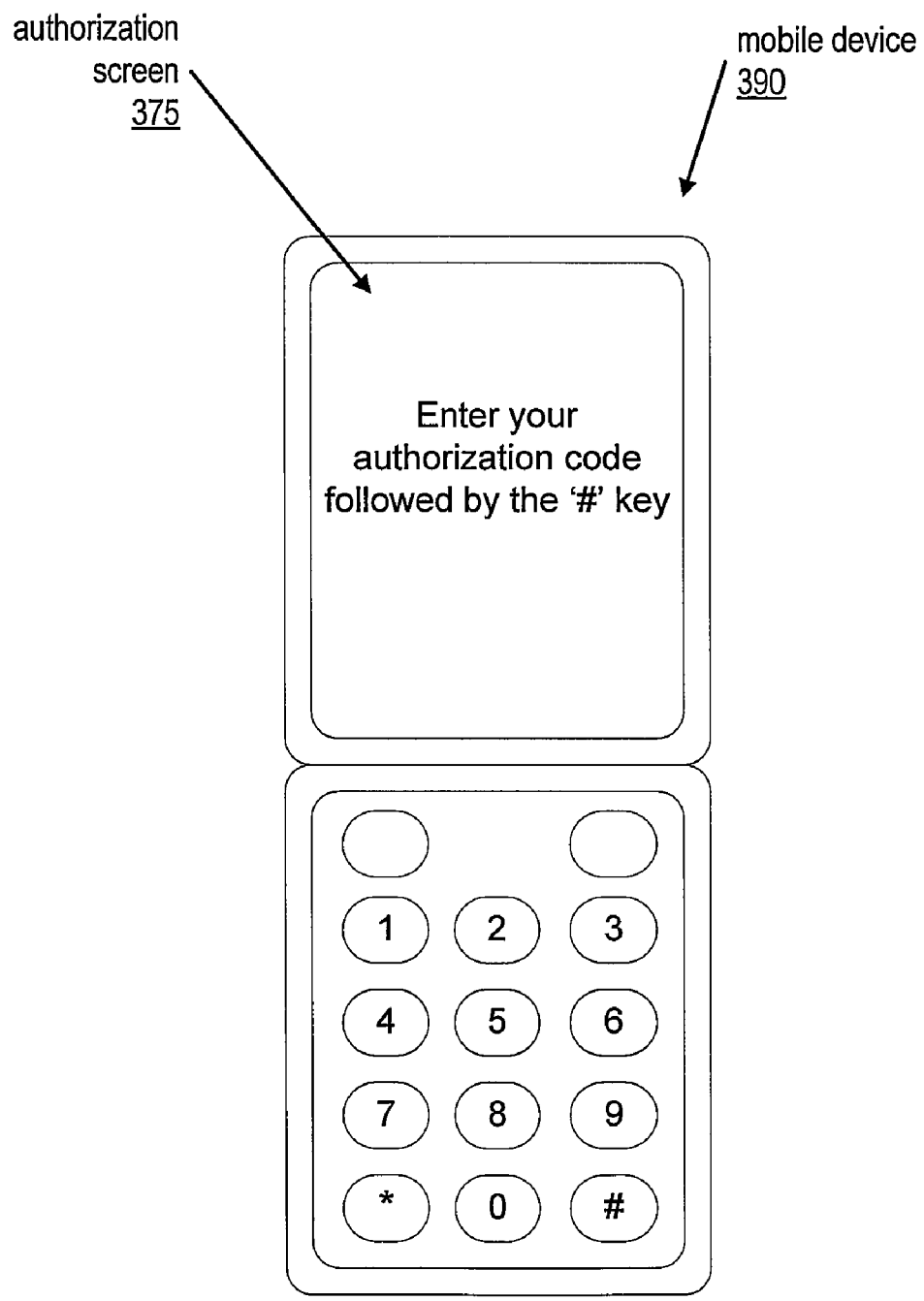

In some embodiments, a mobile communication device used by an approver may include a simpler display and/or interface than display 350 illustrated in FIG. 3A. For example, an approver may respond to an authorization request by sending one or more text messages to a particular phone number or email address, or by replying to a received text message, in some embodiments. FIGS. 3B-3D illustrate exemplary displays on a mobile communication device 390 for use by an approver, according to one such embodiment. FIG. 3B illustrates an exemplary request approval screen 380, in which an authorization request is displayed, along with instructions for providing an answer to the request. FIG. 3C illustrates an exemplary comment screen 385 prompting an approver to enter a comment. This screen may be displayed in response to any answer being entered on request approval screen 380, or in response to an approver selecting "NEED MORE INFORMATION", in different embodiments. FIG. 3D illustrates an exemplary authorization screen 375 prompting an approver to enter his or her authorization code. In some embodiments, this authorization code may be used to authenticate the approver's reply. The number and format of various text messages used by an approver, as well as any keypad commands or functions used by an approver, may in some embodiments be configurable by subscribers.

The authorization service application may in some embodiments be configured to provide a response to the requester when an approver submits his or her authorization reply. In some embodiments, an authorization service application may be configured to send a response message (e.g., an email, text message, or synthesized voice message) to the requester, while in other embodiments the authorization service application may be configured to notify the requester (e.g., through an email, text message or synthesized voice message) that an approver has responded to the authorization request and instructing the requester to log onto the authorization service website to retrieve or view the approver's response.

Figure 4:
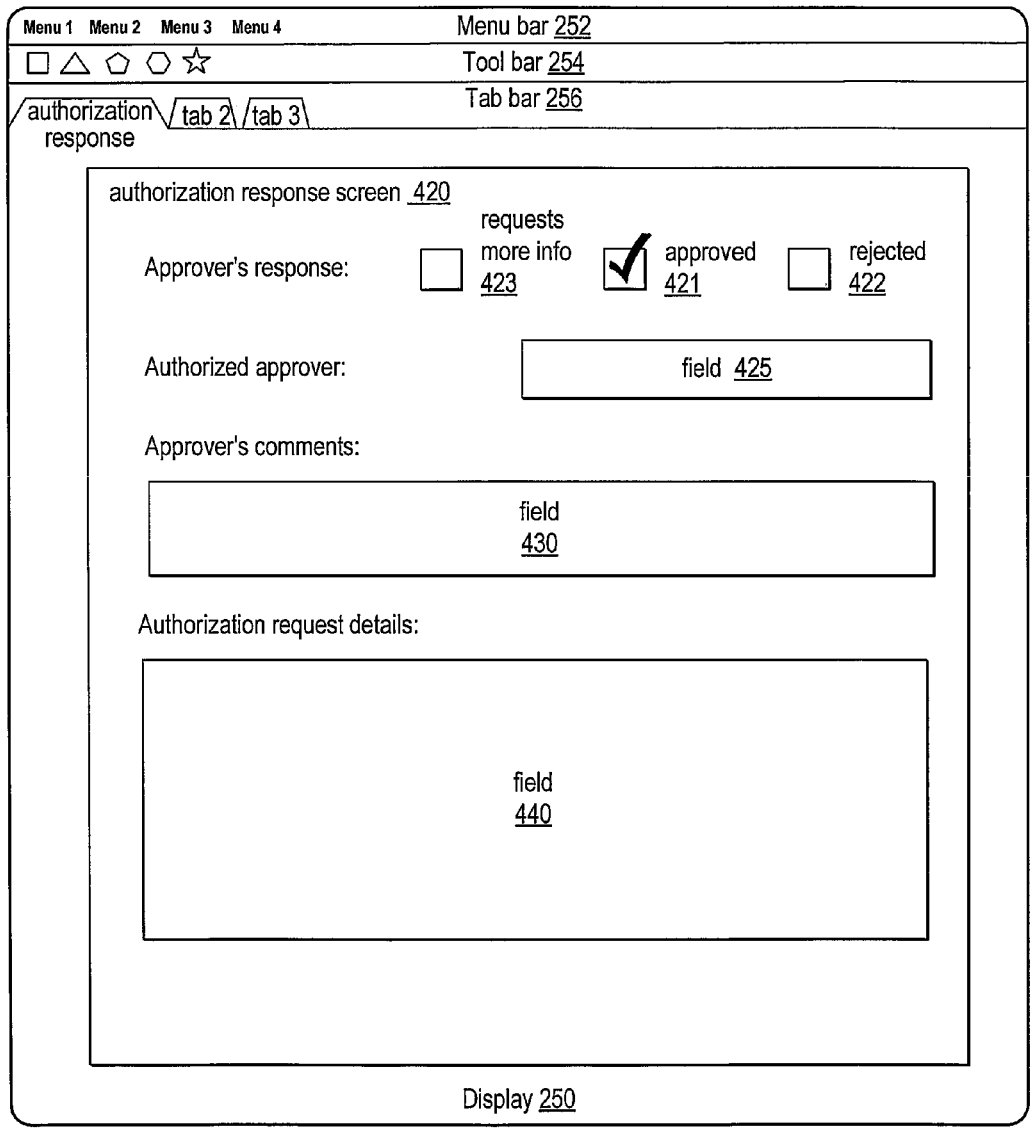
FIG. 4 illustrates an exemplary display and user interface that may be provided by or used with a mobile authorization service, according to various embodiments.

An exemplary authorization response screen is illustrated in FIG. 4. In this example, display 250 may be the same as or similar to display 250 illustrated in FIGS. 2A and 2B, and may include authorization response screen 420 as one of several choices on tab bar 256. As illustrated in FIG. 4, authorization response screen 420 may include several display fields, such as fields 421, 422, 423, 425, 430, and 440. These display screens may indicate the authorization request details (as in 440), the name or identifier of the approver (as in 425), the response (in one of 421, 422, or 423), and/or any comments entered by the approver (e.g., explaining the decision, requesting specific information, or providing additional guidance to the requester.)

As illustrated in FIG. 4, authorization response screen 420 may not include any input fields, in some embodiments. In other embodiments, one or more input fields may allow the requester to add additional information to the authorization request's history or audit log after a response has been received from an approver. For example, an additional field may be provided in which the requester may enter comments responding to an approver's rejection (e.g., acknowledging the rejection, but expressing disagreement with the decision), or in which the requester may enter comments regarding an outcome based on the decision (e.g., the prognosis following an approved medical procedure or the outcome of a business meeting for which an additional expense was approved or rejected.)

A web-based authorization service, as described herein, may include additional display screens not illustrated. For example, one or more help screens or other dialog screens may be provided for guiding a requester or approver through the authorization process. In such embodiments, these dialog screens may present instructions and explanations for the authorization process steps, display fields/screens, and input fields.

While the examples illustrated in FIGS. 2A, 2B, 3A, and 4 involve graphical user interfaces having various input and display fields, inputs and outputs may be provided to an authorization service application using means other than those illustrated. For example, more, fewer, or different types of displays, menus, tabs, and bars may be included in a graphical user interface or other user interface for performing the functionality provided to a computing system of a requesting organization and/or to a mobile communication device of an approver, in various embodiments (e.g., operations may be invoked by selecting an operation from a pull-down menu, selecting one or more radio buttons, entering information in a text field, entering commands on a command line, or using a scripting language or configuration file.) A web-based implementation, for example, may include other types of menus, buttons, scrollbars, and may also include search capabilities for accessing information about specific authorization requests and responses.

As described above, in some embodiments, messages sent to and from an authorization service from an approver and/or requester may be alphanumeric messages (i.e., without graphical content), such as SMS messages from two-way pagers, mobile phones, or PDAs, and the authorization service may parse, generate and/or forward such messages as an intermediary between requesters and approvers.

In yet another embodiment, some or all of the communications described may be implemented as voice messages, and the authorization service may include voice recognition and/or voice synthesis software to analyze, generate and/or forward messages to and from approvers and/or requesters. In general, any suitable user interface of a mobile communication device and/or other computing device may be used to implement providing an authorization request, sending the request to an approver, replying to the request, or responding to a requester, as described herein.

Note also that in various embodiments, some or all of the messages described as being transmitted between a mobile authorization service and a requester or approver may be transmitted securely. Secure transmission may be implemented using a variety of security features and mechanisms, including, but not limited to the use of various encryption schemes, private networks and/or communication channels, or secure socket layers.

As noted above regarding FIG. 1, in some embodiments, information regarding the interactions described above may be captured by the authorization service and may serve compiled into a document detailing the history of an event or an audit log. For example, an audit log for a particular medical authorization request may include a copy of all or a portion of the authorization request (e.g., the name or identifier of the requester, the patient's name, the diagnosis code, the procedure code, and any comments entered by the requester), the name or identifier for each approver to whom the request was sent, the contact information used to send the request to each approver (e.g., the phone number or email address), the response from each approver, any comments entered by each approver, date/time stamps for each of the messages sent and received, and/or the final decision regarding the authorization request.

As described herein, a mobile authorization service may manage various types of data including authorization request data (such as the data described above that may be stored in an audit log, or any other data associated with one or more authorization requests); standard and/or custom documentation and/or attachments; account configuration information for one or more subscribers/customers; standard and/or custom authorization process data, program code, or documentation; standard and/or custom authorization process rules; and contact information and/or information indicating a level of approval authority for one or more individual subscribers/customers and/or groups of subscribers/customers (e.g., corporations and their employees, work teams, non-profit organizations, family members, etc.). In various embodiments, the mobile authorization service may exchange some or all of this information with requesters and/or approvers as part of the authorization process.

Figure 5:
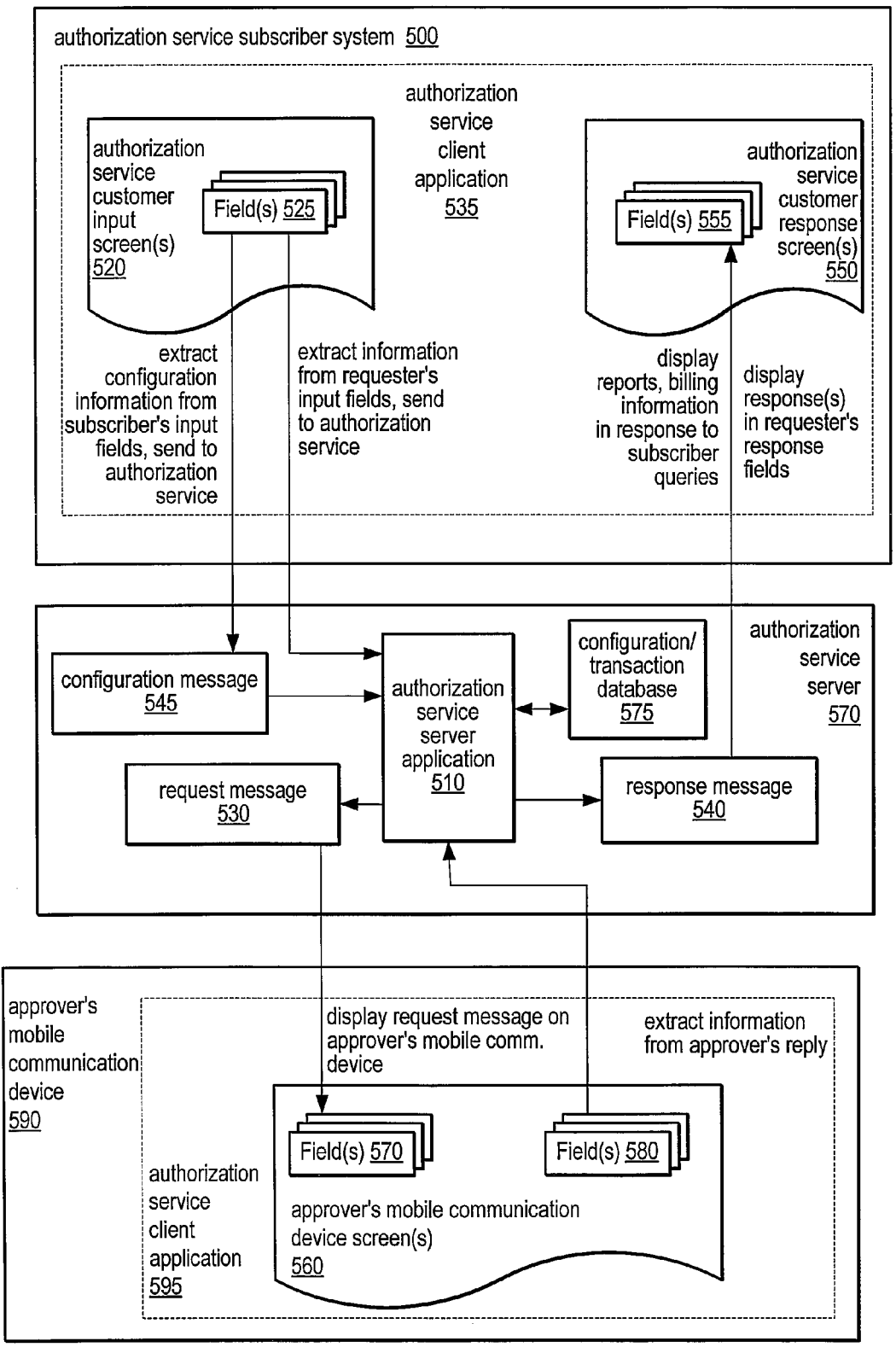
FIG. 5 illustrates a data flow diagram for a mobile authorization service, according to one embodiment.

An exemplary data flow diagram for a mobile authorization service as described herein is illustrated in FIG. 5. In this example, an authorization service subscriber may user computer system 500 to enter configuration information and/or authorization requests, and to display responses to particular authorization requests, and/or responses to other queries regarding one or more authorization requests.

As previously noted, configuration information for an authorization subscriber's account may be entered using an input screen of graphical user interface, such as one of several input screens 520. In this example, configuration information may be extracted from the fields of an input screen 520 by the authorization service client application 535 executing on computer system 500 and sent to authorization service server 570 as a configuration message 545. Authorization service server application 510, executing on authorization service server 570, may be configured to extract configuration information from configuration message 545, to store it in a data store, such as configuration/transaction database 575, to access this information to configure or re-configure a subscription service account for the subscriber, and to access this information when managing authorization transactions on behalf of the subscriber.

In the example illustrated in FIG. 5, authorization requests may be entered by a requesting subscriber using an input screen of a graphical user interface, such as one of several input screens 520. In this example, authorization request information may be extracted from the fields of an input screen 520 by the authorization service client application 535 executing on computer system 500 and sent to authorization service server 570. In other embodiments, a requesting subscriber may log onto authorization service server 570 through a web browser application executing on system 550, rather than executing a client portion of the authorization service application on system 500, and the information may be extracted from an input screen 520 by the authorization server application 510.

As previously noted, an authorization service application (e.g., client application 535 executing on system 500, and/or server application 510 executing on server 570) may be configured to create an authorization request (e.g., an electronic document or "ticket") from the information entered by a subscriber using an authorization request input screen, and may add additional information and/or attachments to the authorization request dependent on the information entered and/or configuration information for the requesting and/or approving subscriber. This authorization request is represented in FIG. 5 as request message 530. Authorization service server application 510, executing on authorization service server 570, may be configured to send request message 530 to an approving subscriber's mobile communication device (e.g., device 590), according to the information entered by the requesting subscriber and/or configuration information for the requesting and/or approving subscriber (e.g., the type of request, a dollar amount, contact information for the approver, etc.) Authorization service server application 510 may also be configured to store all or a portion of request message 530 (and/or the authorization request information from which it was created) in a data store, such as configuration/transaction database 575.

An authorization service client application, such as authorization service client application 595, executing on the approving subscriber's mobile communication device may be configured to display all or a portion of request message 530 on the approving subscriber's mobile communication device 590. In the example illustrated in FIG. 5, request message 530 may be displayed in one or more of display fields 570 of an input/output screen on the mobile communication device 590 (e.g., one of device screens 560). In other embodiments, the approver's mobile communication device 590 may receive and/or display all or a portion of request message 530 using another type of application executing on mobile communication device 590. For example, request message 530 may be a text message received from authorization service server 570 and may be received and displayed by a standard text messaging application executing on mobile communication device 590. In another example, mobile communication device 590 may connect to authorization application service server 570 through a standard web browsing application executing on mobile communication device 590 to allow the approving subscriber to view request message 530 (e.g., in response to receiving a phone call or a text message indicating that the approving subscriber has a pending authorization request.)

In the example illustrated in FIG. 5, the approving subscriber may provide a response to the authorization request by entering data in one or more of input fields 580 of a display screen 560 through authorization service client application 595. In other embodiments, the approving subscriber may enter a response to the authorization request by connecting to the authorization application service server 570 through a standard web browsing application executing on mobile communication device 590 and entering a response. In still other embodiments, the approving subscriber may enter a response to the authorization request by sending a text message (or text message reply) to the authorization service server 570. As previously described, the approving subscriber may in some embodiments include comments and/or requests for additional information in his or her response in addition to (or instead of) including an indication of approval or rejection of the authorization request in the response.

As illustrated in FIG. 5, authorization service server application 510 may receive the response from the approving subscriber and may generate a response message 540 to be provided to the requesting subscriber. In other embodiments, authorization service server application 510 may generate a response message 540 from a response entered on authorization service server 570 by an approving subscriber by logging into server 570 to provide the response (e.g., using a web browser on mobile communication device 590 to access authorization service server application 510). Response message 540 may be provided to the requesting subscriber by sending all or a portion of the message to authorization service subscriber system 500 (e.g., as an email, text message, or other data transmission), in some embodiments. As illustrated in FIG. 5, in such embodiments, authorization service client application 535 may be configured to receive the response message 540 and to display all or a portion of it in fields 555 of response screens 550.

In some embodiments, authorization service server application 510 may be configured to store all or a portion of response message 540 (and/or the information used to generate it) in a data store, such as configuration/transaction database 575. In some embodiments, response message 540 may be provided to the requesting subscriber by updating information associated with the request in a data store on server 570 so that the requesting subscriber may view the response by logging onto server 570 using a web browser application and accessing the data store (e.g., configuration/transaction database 575) to retrieve the information. In various embodiments, the requesting subscriber may log onto server 570 periodically to check the status of a pending request, and/or may log onto server 570 in response to receiving a message from server 570 indicating a change of status for a pending request.

In addition to providing input and output screens for configuration information and specific authorization requests, authorization service client applications 535 and/or 595 may be configured to allow a subscriber to query authorization service server 570 for information. Subscribers may query server 570 to obtain status for one or more pending authorization requests, to obtain reports regarding one or more pending or completed authorization transactions (e.g., for a group of requests for a particular time period, work group, project, patient, etc.), or to obtain account information (e.g., configuration information, billing information, etc.) In some embodiments, the results of these queries may be returned to authorization service client applications 535 and/or 595 for display on screens 550 and/or 560.

In some embodiments, a billing agent executing on authorization service server 570 (e.g., a module of authorization service server application 510) may be configured to send billing information (e.g., current balance, amounts due, usage information) to subscribers on a periodic or event-driven basis. For example, some subscriber accounts may be configured such that the subscriber receives a monthly bill, while others may be configured such that the subscriber receives a bill only when the authorization service is used to manage one or more authorization transactions within a given time period. Still other subscriber accounts may be configured for automatic payments (e.g., using a pre-arranged on-line banking draft) and a billing agent may be configured to send billing information to subscribers for tracking/auditing purposes only.

Exemplary Systems

Figure 6:
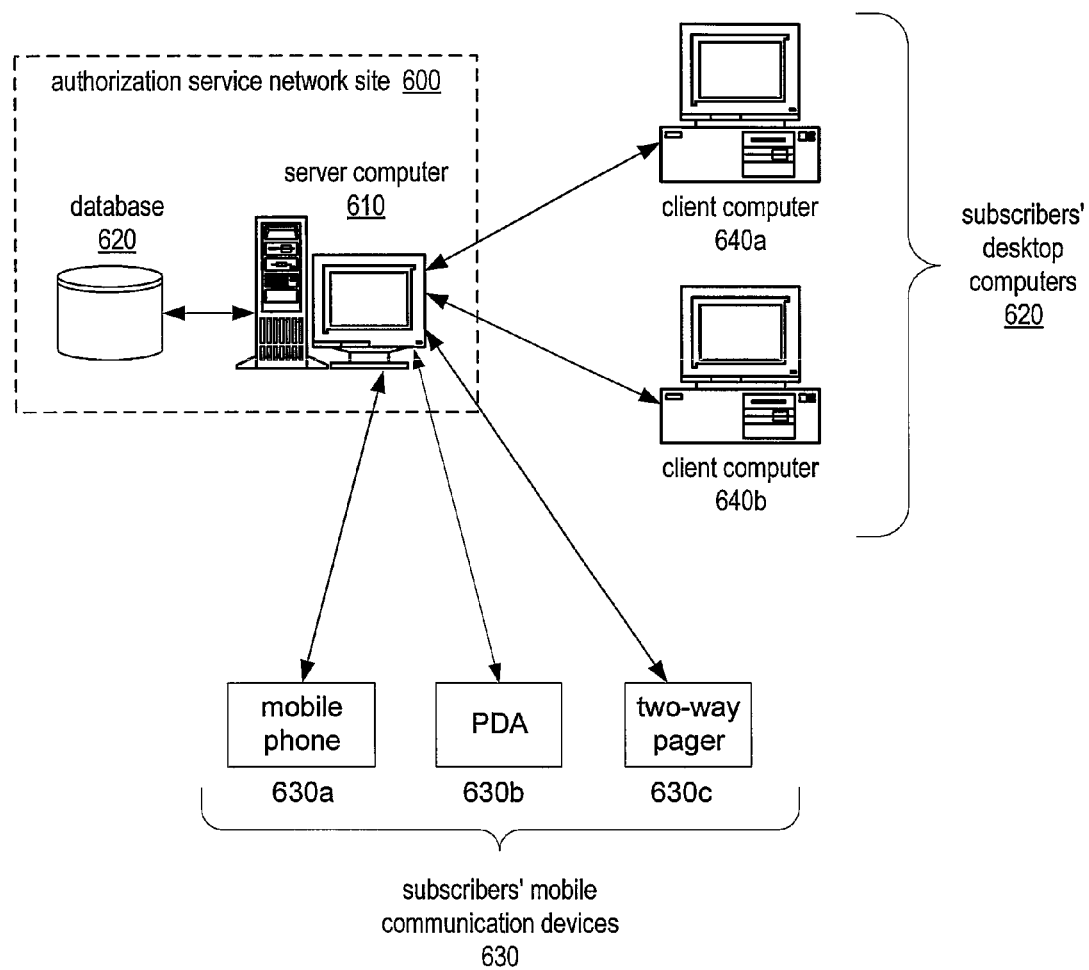
FIGS. 6 and 7 illustrate exemplary computing systems on which embodiments may be implemented.

As described herein, a mobile authorization service may be implemented as one or more authorization service applications executing on one or more computing systems to facilitate an approver responding to various types of authorization requests remotely. One embodiment of a system implementing such a service is illustrated in FIG. 6. In this example, a mobile authorization service may be hosted through an authorization service network site 600. As illustrated in FIG. 6, a server computer 610 and database 620 may be co-located at the site and may be accessed via a network (e.g., the Internet) by various subscriber devices.

As illustrated in FIG. 6, subscriber devices suitable for accessing the authorization service may include one or more desktop computers 640, such as client computing devices 640a and 640b, and/or various types of mobile communication devices 630, such as mobile phone 630a, PDA 630b, and/or two-way pager 630c. In various embodiments, any of these subscriber devices, or any other computing devices capable of connecting to network site 600 and/or sending or receiving data to and from network site 600 may implement the functionality described herein regarding requesting and/or approving authorization requests using a mobile authorization service as described herein.

Figure 7:
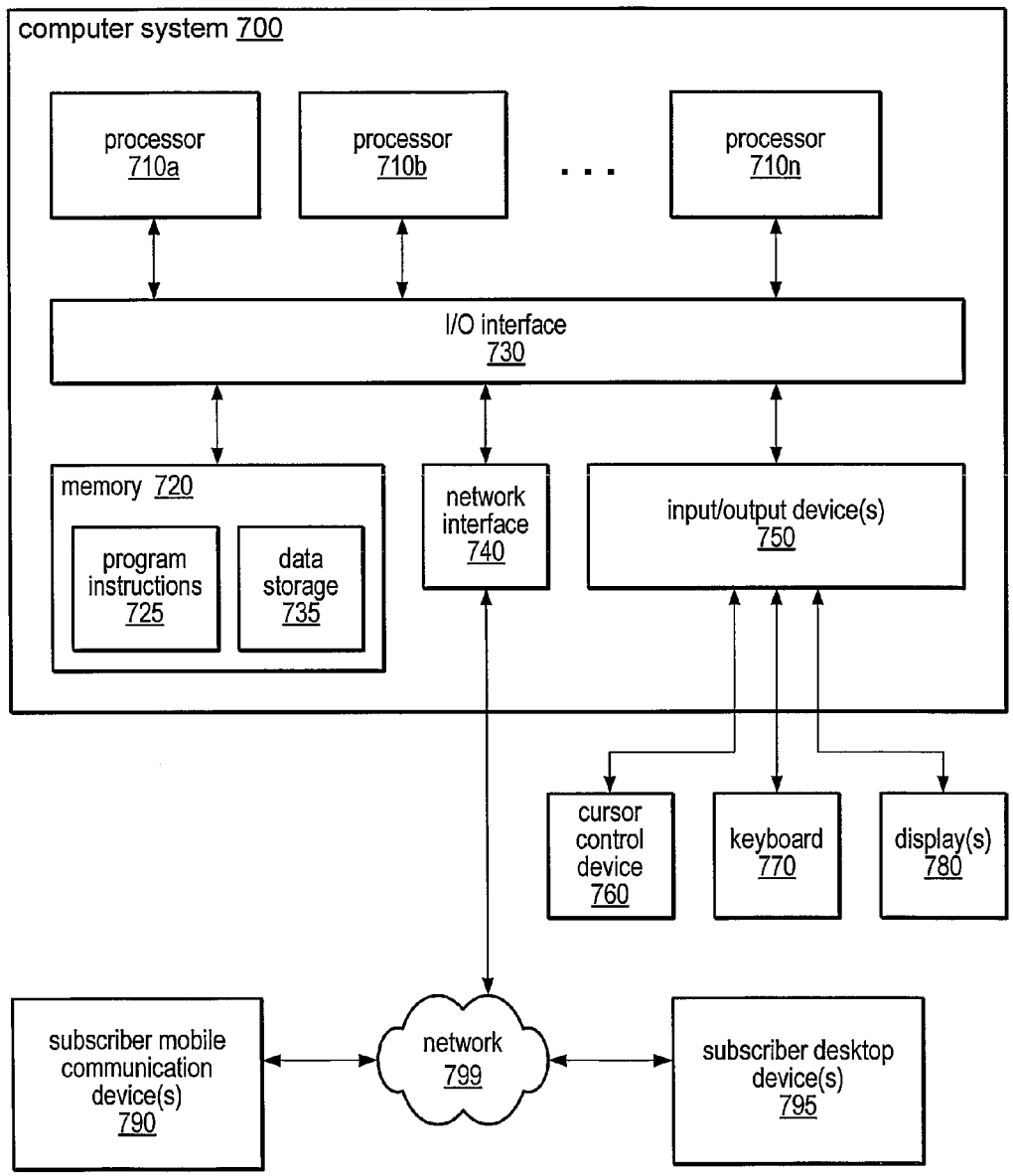

An exemplary computer system 700 suitable for implementing the mobile authorization service described herein is illustrated in more detail in FIG. 7. Computer system 700 may represent an authorization service server or any of one or more client computing systems used to remotely initiate or respond to an authorization request. For example, in some embodiments one or more of subscriber mobile communication devices 790 and/or subscriber desktop devices 795 may include the same or similar components and functionality as computer system 700. In other embodiments, subscriber mobile communication devices 790 and/or subscriber desktop devices 795 may include different components and/or functionality than computer system 700, or a subset of the components and functionality described herein regarding computer system 700.

In the illustrated embodiment, computer system 700 includes one or more processors 710 coupled to a system memory 720 via an input/output (I/O) interface 730. Computer system 700 further includes a network interface 740 coupled to I/O interface 730, and one or more input/output devices 750, such as cursor control device 760, keyboard 770, and display(s) 780. In some embodiments, it is contemplated that embodiments may be implemented using a single instance of computer system 700, in communication with other types of devices, while in other embodiments multiple such systems, or multiple nodes making up computer system 700, may be configured to host different portions or instances of embodiments. For example, in one embodiment a client portion of an authorization service application may be implemented via one or more nodes of computer system 700 that are distinct from a node implementing a server portion of the authorization service application. As previously noted, in some embodiments, the service may be implemented in a peer-to-peer environment, rather than in a system employing a fixed client/server model, with one or more of the peer nodes hosting the authorization service and one or more peer nodes accessing the service as subscriber devices.

In various embodiments, computer system 700 may be a uniprocessor system including one processor 710, or a multiprocessor system including several processors 710 (e.g., two, four, eight, or another suitable number). Processors 710 may be any suitable processor capable of executing instructions. For example, in various embodiments processors 710 may be general-purpose or embedded processors implementing any of a variety of instruction set architectures (ISAs), such as the x86, PowerPC, SPARC, or MIPS ISAs, or any other suitable ISA. In multiprocessor systems, each of processors 710 may commonly, but not necessarily, implement the same ISA.

System memory 720 may be configured to store program instructions and/or data accessible by processor 710. In various embodiments, system memory 720 may be implemented using any suitable memory technology, such as static random access memory (SRAM), synchronous dynamic RAM (SDRAM), nonvolatile/Flash-type memory, or any other type of memory. In the illustrated embodiment, program instructions and data implementing desired functions, such as those described above regarding an authorization service application and associated configuration and authorization transaction data, are shown stored within system memory 720 as program instructions 725 and data storage 735, respectively. In other embodiments, program instructions and/or data may be received, sent or stored upon different types of computer-accessible media or on similar media separate from system memory 720 or computer system 700. Generally speaking, a computer-accessible medium may include storage media or memory media such as magnetic or optical media, e.g., disk or CD/DVD-ROM coupled to computer system 700 via I/O interface 730. Program instructions and data stored via a computer-accessible medium may be transmitted by transmission media or signals such as electrical, electromagnetic, or digital signals, which may be conveyed via a communication medium such as a network and/or a wireless link, such as may be implemented via network interface 740.

In one embodiment, I/O interface 730 may be configured to coordinate I/O traffic between processor 710, system memory 720, and any peripheral devices in the device, including network interface 740 or other peripheral interfaces, such as input/output devices 750. In some embodiments, I/O interface 730 may perform any necessary protocol, timing or other data transformations to convert data signals from one component (e.g., system memory 720) into a format suitable for use by another component (e.g., processor 710). In some embodiments, I/O interface 730 may include support for devices attached through various types of peripheral buses, such as a variant of the Peripheral Component Interconnect (PCI) bus standard or the Universal Serial Bus (USB) standard, for example. In some embodiments, the function of I/O interface 730 may be split into two or more separate components, such as a north bridge and a south bridge, for example. Also, in some embodiments some or all of the functionality of I/O interface 730, such as an interface to system memory 720, may be incorporated directly into processor 710.

Network interface 740 may be configured to allow data to be exchanged between computer system 700 and other devices attached to a network 799, such as other computer systems, subscriber devices 790 and/or 795, or between nodes of computer system 700. In various embodiments, network interface 740 may support communication via wired or wireless general data networks, such as any suitable type of Ethernet network, for example; via telecommunications/telephony networks such as analog voice networks or digital fiber communications networks; via storage area networks such as Fibre Channel SANs, or via any other suitable type of network and/or protocol.

Input/output devices 750 may, in some embodiments, include one or more display terminals, keyboards, keypads, touchpads, scanning devices, voice or optical recognition devices, or any other devices suitable for entering or retrieving data by one or more computer system 700. Multiple input/output devices 750 may be present in computer system 700 or may be distributed on various nodes of computer system 700. In some embodiments, similar input/output devices may be separate from computer system 700 and may interact with one or more nodes of computer system 700 through a wired or wireless connection, such as over network interface 740.

As shown in FIG. 7, memory 720 may include program instructions 725, configured to implement embodiments of an authorization service application as described herein, and data storage 735, comprising various databases and/or other data structures accessible by program instructions 725. In one embodiment, program instructions 725 may implement a server portion of an authorization application, including one or more authorizing agents and/or billing agents, as described herein. In other embodiments, program instructions 725 may implement a client portion of an authorization application and/or other applications suitable for carrying out the functionality of a subscriber device 790 and/or 795. For example, program instructions 725 may include instructions configured to implement a web browser application, a text messaging application, voice recognition or synthesis software, or any other applications suitable for facilitating communication between an authorization service and a subscriber device. In one embodiment, data storage 735 may be configured to implement a database, such as configuration/transaction database 575, as described herein. Data storage 735 may in some embodiments be configured to store various request messages 530, response messages 540, and/or configuration messages 545. In other embodiments, additional or different software elements and data may be included in memory 720.

Those skilled in the art will appreciate that computer system 700 is merely illustrative and is not intended to limit the scope of the present invention. In particular, the computer system and devices may include any combination of hardware or software that can perform the indicated functions, including computers, network devices, internet appliances, PDAs, wireless phones, pagers, etc. Computer system 700 may also be connected to other devices that are not illustrated. In addition, the functionality provided by the illustrated components may in some embodiments be combined in fewer components or distributed in additional components. Similarly, in some embodiments, the functionality of some of the illustrated components may not be provided and/or other additional functionality may be available.

Those skilled in the art will also appreciate that, while various items are illustrated as being stored in memory or on storage while being used, these items or portions of them may be transferred between memory and other storage devices for purposes of memory management and data integrity. Alternatively, in other embodiments some or all of the software components may execute in memory on another device and communicate with the illustrated computer system via inter-computer communication. Some or all of the system components or data structures may also be stored (e.g., as instructions or structured data) on a computer-accessible medium or a portable article to be read by an appropriate drive, various examples of which are described above. In some embodiments, instructions stored on a computer-accessible medium separate from computer system 700 may be transmitted to computer system 700 via transmission media or signals such as electrical, electromagnetic, or digital signals, conveyed via a communication medium such as a network and/or a wireless link. Various embodiments may further include receiving, sending or storing instructions and/or data implemented in accordance with the foregoing description upon a computer-accessible medium. Accordingly, the present invention may be practiced with other computer system configurations.

Various embodiments may further include receiving, sending or storing instructions and/or data implemented in accordance with the foregoing description upon a computer-accessible medium. Generally speaking, a computer-accessible medium may include storage media or memory media such as magnetic or optical media, e.g., disk or DVD/CD-ROM, volatile or non-volatile media such as RAM (e.g. SDRAM, DDR, RDRAM, SRAM, etc.), ROM, etc., as well as transmission media or signals such as electrical, electromagnetic, or digital signals, conveyed via a communication medium such as network and/or a wireless link.

Note that the user interface mechanisms and elements as illustrated and described are exemplary and are not intended to be limiting, and various modifications to or variations of the mechanisms and elements are possible, as are alternative user interface mechanisms and elements that are configured to perform similar functions.

Note also that the methods described herein may be used by an individual authorization service subscriber having a personal authorization service subscription, or by a representative of a corporation having a corporate subscription to manage one or more authorization requests on behalf of one or more other employees of the corporation, in various embodiments.

In some embodiments, the remote authorization service described herein may be configured to interact with a healthcare management application. A healthcare management application may in some embodiments provide a consumer with a framework and tools for collecting, organizing, and managing data related to their health history; past, current and future health services; health insurance plan(s) (e.g., what services are covered, coverage limits, claims status, and explanations of benefits); and finances related to healthcare (e.g., health insurance premiums, deductibles, co-payments, benefit payments, reimbursements from one or more Flexible Spending Accounts, Health Reimbursement Accounts, or Health Savings Accounts, maximum out-of-pocket expenses, and maximum lifetime benefits.) For example, a healthcare management application may be configured to provide a consumer with a comprehensive and detailed health history, or may allow the consumer to extract and/or analyze his or her data regarding a particular health condition or event (e.g., an injury or illness) or a particular healthcare-related service (e.g., a particular diagnostic exam or a course of treatment for a chronic condition.)

A healthcare management application may in some embodiments be implemented as a web-based service to which consumers and/or employers may subscribe. In other embodiments, it may be implemented as a stand-alone application, such as one installed and executed on a desktop computer by a consumer. In some embodiments, a healthcare management application may include both a locally installed application (i.e., a client portion) and a remote, web-based application (i.e., a server portion). For example, in one embodiment, a consumer may enter healthcare-related information on a locally installed client application and then may upload the information to a healthcare management service server for secure storage and/or further analysis.

In various embodiments, a healthcare management application may receive information from one or more of: a consumer, one or more healthcare providers, one or more health plan administrators (e.g., health insurance representatives), and one or more financial institutions. The information received and/or managed by a healthcare management application may be formatted according to a standard data exchange format, in some embodiments.

A healthcare management application may in some embodiments maintain healthcare-related information in one or more databases (or in other suitable formats) in a local or remote memory, or in a combination of the two. For example, a database located on a healthcare management service server may be configured to securely store healthcare-related information for multiple individual consumers or for employees of one or more corporations subscribing to the healthcare management service, while a database stored locally on a consumer's computing system may include only his or her own personal healthcare-related data.

The information managed by a healthcare management application may in some embodiments be extracted for use by other applications, such as the mobile authorization service application described herein. For example, in one embodiment, the authorization service application may be configured to extract a health history from the healthcare management application and provide this to an approver as an attachment to a medical authorization request.

Similarly, information may be extracted from other applications for management, organization, and/or analysis by a healthcare management application. In one embodiment, the authorization service application may be configured to provide authorization transaction information, such as that described as being stored in configuration/transaction database 575, to a healthcare management application to be managed along with other healthcare-related information. For example, a log of an authorization transaction for a request for emergency surgery (including a diagnosis code, procedure code, etc.) may be provided to a healthcare management application and associated with other information about the surgery, such as previous treatments related to the same condition, insurance information, healthcare provider information, results of the surgery, ongoing treatment options, etc.

The methods may be implemented in software, hardware, or a combination thereof, in different embodiments. In addition, the order of method may be changed, and various elements may be added, reordered, combined, omitted, modified, etc. Various modifications and changes may be made as would be obvious to a person skilled in the art having the benefit of this disclosure.

Realizations in accordance with the present invention have been described in the context of particular embodiments. These embodiments are meant to be illustrative and not limiting. Many variations, modifications, additions, and improvements are possible. Accordingly, plural instances may be provided for components described herein as a single instance. Boundaries between various components, operations and data stores are somewhat arbitrary, and particular operations are illustrated in the context of specific illustrative configurations. Other allocations of functionality are envisioned and may fall within the scope of claims that follow. Finally, structures and functionality presented as discrete components in the exemplary configurations may be implemented as a combined structure or component. These and other variations, modifications, additions, and improvements may fall within the scope of the invention as defined in the claims that follow.

What is claimed is:

1. A non-transitory computer-readable storage medium, comprising program instructions computer-executable, to implement a method, comprising:
   receiving an authorization request from a requester;
   determining at least one user approver authorized to approve the authorization request and the number of approvers required to approve the request, wherein to determine the at least one user approver, consideration is given to the identity of a third party optionally identified in the request on whose behalf the authorization request is made, the location of the requestor, the location of individual potential approvers, and the requestor's job grade;
   sending a request message to at least the number of required user approvers, the request message including an indicator of priority or urgency, wherein sending a request message to at least the number of required user approvers comprises contacting at least one of the user approvers for both a verbal authorization and an authenticated approval through the network, wherein if the number of approvers required for the given authorization request is more than one, the more than one required approvers operate to approve or deny the request in parallel with the other approvers of the more than one required approvers;
   sending, if one or more of the user approver's answers includes a denial of the request, the request to one or more additional user approvers authorized to approve the request;
   wherein at least one of said receiving an authorization request, said sending a response, said sending a request message, and said receiving a reply message comprise communicating via a mobile communication device.

2. The method of claim 1, wherein the approver's answer comprises one or more of: an approval, a rejection, a request for more information, and a comment.

3. The method of claim 1, wherein the reply message comprises authentication information identifying the approver, and wherein said authenticating the reply message comprises comparing the authentication information to information previously stored for use in authenticating messages from one or more approvers.

4. The method of claim 3, wherein the authentication information comprises one or more of: a personal identification number (PIN), a digital signature, an audio file comprising a voice command, a digital representation of a scanned thumbprint or retina, or an image file comprising a scanned thumbprint or retina.

5. The method of claim 1, further comprising storing information regarding the authorization request.

6. The method of claim 5, wherein said storing information regarding the authorization request comprises storing one or more of: the authorization request, the request message, the reply message, and the response.

7. The method of claim 1, wherein the authorization request comprises one or more of: an indicator of a request type, an indicator of a requested action, a dollar amount, an account number, an identifier of the requester, and an identifier of an approver.

8. The method of claim 1, further comprising determining the approver to whom the request message is sent dependent on information comprised in the authorization request other than an identifier of the approver.

9. The method of claim 1, further comprising creating the request message dependent on information comprised in the authorization request, wherein the request message comprises additional information not comprised in the authorization request.

10. The method of claim 1, further comprising accessing configuration information associated with the requestor, wherein said sending a request message and said authenticating the reply message are performed in accordance with said configuration information.

11. A computing system, comprising:
    one or more processors;
    memory coupled to the one or more processors, wherein the memory is configured to store program instructions executable by the one or more processors to implement a mobile authorization service application configured to:
    receive an authorization request from a requester;
    determine at least one user approver authorized to approve the authorization request and the number of approvers required to approve the request, wherein to determine the at least one user approver, consideration is given to the identity of a third party optionally identified in the request on whose behalf the authorization request is made, the location of the requestor, the location of individual potential approvers, and the requestor's job grade;
    send a request message to at least the number of required user approvers, the request message including an indicator of priority or urgency, wherein sending a request message to at least the number of required user approvers comprises contacting at least one of the user approvers for both a verbal authorization and an authenticated approval through the network, wherein if the number of approvers required for the given authorization request is more than one, the more than one required approvers operate to approve or deny the request in parallel with the other approvers of the more than one required approvers;

receive a reply message from each of the user approvers that were sent the request message in addition to receiving the verbal reply from the particular one of the user approvers requested to do so, the reply message indicating the particular user approver's answer;

authenticate each reply message based on authorization information and the location of the approver at the time of the approval; and send a response to the requester indicating each user approver's answer;

send, if one or more of the user approver's answers includes a denial of the request, the request to one or more additional user approvers authorized to approve the request;

wherein at least one of said receiving an authorization request, said sending a response, said sending a request message, and said receiving a reply message comprise communicating via a mobile communication device.

12. The system of claim 11, wherein the approver's answer comprises one or more of: an approval, a rejection, a request for more information, and a comment.

13. The system of claim 11, wherein the reply message comprises authentication information identifying the approver, and wherein to authenticate the reply message, the authorization service application is further configured to compare the authentication information to information comprised in the memory for authenticating messages from subscribers of an authorization service.

14. The system of claim 13, wherein the authentication information comprises one or more of: a personal identification number (PIN), a digital signature, an audio file comprising a voice command, a digital representation of a scanned thumbprint or retina, or an image file comprising a scanned thumbprint or retina.

15. The system of claim 11, wherein the authorization request comprises one or more of: an indicator of a request type, an indicator of a requested action, a dollar amount, an account number, an identifier of the requester, and an identifier of an approver.

16. The system of claim 11, wherein the authorization service application is further configured to determine the approver to whom the request message is sent dependent on information comprised in the authorization request other than an identifier of the approver.

17. The system of claim 11, wherein the authorization service application is further configured to store information regarding the authorization request in the memory.

18. The system of claim 17, wherein to store information regarding the authorization request, the authorization service application is further configured to store one or more of: the authorization request, the request message, the reply message, and the response.

19. The system of claim 11, wherein the authorization service application is further configured to create the request message dependent on information comprised in the authorization request, wherein the request message comprises additional information not comprised in the authorization request.

20. The system of claim 11, wherein the authorization service application is further configured to access configuration information associated with the requestor, wherein said sending a request message and said authenticating the reply message are performed in accordance with said configuration information.

21. A non-transitory computer-readable storage medium, comprising program instructions computer-executable to implement a mobile authorization service application configured to:

receive an authorization request from a requester; determine at least one user approver authorized to approve the authorization request and the number of approvers required to approve the request, wherein to determine the at least one user approver, consideration is given to the identity of a third party optionally identified in the request on whose behalf the authorization request is made, the location of the requestor, the location of individual potential approvers, and the requestor's job grade;

send a request message to at least the number of required user approvers, the request message including an indicator of priority or urgency, wherein sending a request message to at least the number of required user approvers comprises contacting at least one of the user approvers for both a verbal authorization and an authenticated approval through the network, wherein if the number of approvers required for the given authorization request is more than one, the more than one required approvers operate to approve or deny the request in parallel with the other approvers of the more than one required approvers;

receive a reply message from each of the user approvers that were sent the request message in addition to receiving the verbal reply from the particular one of the user approvers requested to do so, the reply message indicating the particular user approver's answer;

authenticate each reply message based on authorization information and the location of the approver at the time of the approval; and send a response to the requester indicating each user approver's answer;

sending, if one or more of the user approver's answers includes a denial of the request, the request to one or more additional user approvers authorized to approve the request; wherein at least one of said receiving an authorization request, said sending a response, said sending a request message, and said receiving a reply message comprise communicating via a mobile communication device.

22. The storage medium of claim 21, wherein the approver's answer comprises one or more of: an approval, a rejection, a request for more information, and a comment.

23. The storage medium of claim 21, wherein the reply message comprises authentication information identifying the approver, and wherein to authenticate the reply message, the authorization service application is further configured to compare the authentication information to information maintained by the authorization service application for authenticating messages from subscribers of the authorization service.

24. The storage medium of claim 23, wherein the authentication information comprises one or more of: a personal identification number (PIN), a digital signature, an audio file comprising a voice command, a digital representation of a scanned thumbprint or retina, or an image file comprising a scanned thumbprint or retina.

25. The storage medium of claim 21, wherein the authorization request comprises one or more of: an indicator of a request type, an indicator of a requested action, a dollar amount, an account number, an identifier of the requester, and an identifier of an approver.

26. The storage medium of claim 21, wherein the authorization service application is further configured to determine the approver to whom the request message is sent dependent on information comprised in the authorization request other than an identifier of the approver.

27. The storage medium of claim 21, wherein the authorization service application is further configured to store information regarding the authorization request in the memory.

28. The storage medium of claim 27, wherein to store information regarding the authorization request, the authorization service application is further configured to store one or more of: the authorization request, the request message, the reply message, and the response.

29. The storage medium of claim 21, wherein the authorization service application is further configured to create the request message dependent on information comprised in the authorization request, wherein the request message comprises additional information not comprised in the authorization request.

30. The storage medium of claim 21, wherein the authorization service application is further configured to access configuration information associated with the requestor, wherein said sending a request message and said authenticating the reply message are performed in accordance with said configuration information.

* * * * *

UNITED STATES PATENT AND TRADEMARK OFFICE
CERTIFICATE OF CORRECTION

| | | |
|---|---|---|
| PATENT NO. | : 8,014,756 B1 | Page 1 of 1 |
| APPLICATION NO. | : 11/680402 | |
| DATED | : September 6, 2011 | |
| INVENTOR(S) | : Kenneth Henderson | |

It is certified that error appears in the above-identified patent and that said Letters Patent is hereby corrected as shown below:

In the Claims

In Column 27, after Line 67, insert:

--receiving a reply message from each of the user approvers that were sent the request message in addition to receiving the verbal reply from the particular one of the user approvers requested to do so, the reply message indicating the particular user approver's answer;

authenticating each reply message based on authorization information and the location of the approver at the time of the approval; and sending a response to the requester indicating each user approver's answer;--

Signed and Sealed this
Twenty-ninth Day of October, 2013

Teresa Stanek Rea
*Deputy Director of the United States Patent and Trademark Office*